(12) United States Patent
Wexselblatt et al.

(10) Patent No.: US 9,133,231 B2
(45) Date of Patent: Sep. 15, 2015

(54) COMPOUNDS FOR TREATING BACTERIAL INFECTIONS

(75) Inventors: Ezequiel Wexselblatt, Beit Zayit (IL); Joshua Katzhendler, Jerusalem (IL); Ilana Kaspy, Givat Zeev (IL); Gad Glaser, Jerusalem (IL); Roee Vidavski, Rehovot (IL); Hafiz Mawasi, Baqa al-Garbiya (IL); Sigal Ben Yehuda, Jerusalem (IL); Yaara Oppenheimer-Shaanan, Bnei-Ream (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 229 days.

(21) Appl. No.: 13/813,726

(22) PCT Filed: Aug. 3, 2011

(86) PCT No.: PCT/IL2011/000629
§ 371 (c)(1),
(2), (4) Date: Apr. 26, 2013

(87) PCT Pub. No.: WO2012/017434
PCT Pub. Date: Feb. 9, 2012

(65) Prior Publication Data
US 2013/0203694 A1  Aug. 8, 2013

Related U.S. Application Data

(60) Provisional application No. 61/370,229, filed on Aug. 3, 2010, provisional application No. 61/431,902, filed on Jan. 12, 2011.

(51) Int. Cl.
*C07H 19/20* (2006.01)
*A61K 31/708* (2006.01)
*C07H 19/173* (2006.01)
*C07H 19/16* (2006.01)

(52) U.S. Cl.
CPC .............. *C07H 19/20* (2013.01); *A61K 31/708* (2013.01); *C07H 19/16* (2013.01); *C07H 19/173* (2013.01)

(58) Field of Classification Search
CPC ...... C07H 19/20; C07H 19/16; C07H 19/173; A61K 31/708
See application file for complete search history.

(56) References Cited

U.S. PATENT DOCUMENTS

2005/0074771 A1   4/2005  Cook et al.

FOREIGN PATENT DOCUMENTS

WO    2009/116044 A2    9/2009

OTHER PUBLICATIONS

Hogg et al., Cell, 2004, 117, p. 57-68.*
Shutes et al., Biochemistry, 2002, 41, p. 3828-3835.*
Berge et al., (1977) Pharmaceutical Salts. J Pharm Sci 66(1): 1-19.
Cashel et al. (1969) Two Compounds implicated in the Function of the RC Gene of *Escherichia coli*. Nature 221 (5183): 838-841.
Cashel et al., (1969) An Improved Method for Thin-Layer Chromatography of Nucleotide Mixtures Containing 32P-Labelled Orthophosphate. J Chromatog 40(1): 103-109.
Cashel et al., (1970) The Control of Ribonucleic Acid Synthesis in *Escherichia coli*: V. Characterization of a Nucleotide Associated with the Stringent Response. J Biol Chem 245(9): 2309-2318.
Errington (2003) Regulation of Endospore Formation in *Bacillus subtilis*. Nat Rev Microbiol 1(2): 117-126.
Freese et al., (1979) Partial Purine Deprivation Causes Sporulation of *Bacillus subtilis* in the Presence of Excess Ammonia, Glucose, and Phosphate. J Gen Microbiol 115(1): 193-205.
Gentry et al., (1993) Synthesis of the Stationary-Phase Sigma Factor sigma s is Positively Regulated by ppGpp. J Bacteriol 175(24): 7982-7989.
Gentry et al. (1995) Cellular Localization of the *Escherichia coli* SpoT Protein. J Bacteriol 177(13): 3890-3893.
Gentry et al., (2000) The rel Gene is Essential for In Vitro Growth of *Staphylococcus aureus*. J Bacteriol 182(17): 4995-4997.
Givens et al., (2004) Inducible Expression, Enzymatic Activity, and Origin of Higher Plant Homologues of Bacterial RelA/SpoT Stress Proteins in *Nicotiana tabacum*. J Biol Chem 279(9): 7495-7504.
Gropp et al., (2001) Regulation of *Escherichia coli* RelA Requires Oligomerization of the C-Terminal Domain. J Bacteriol 183(2): 570-579.
Harris et al., (1998) The guanosine nucleotide (p)ppGpp initiates development and A-factor production in *Myxococcus xanthus*. Genes & Dev 12(7): 1022-1035.
Haseltine et al. (1973) Synthesis of Guanosine Tetra- and Pentaphosphate Requires the Presence of a Codon-Specific, Uncharged Transfer Ribonucleic Acid in the Acceptor Site of Ribosomes. Proc Natl Acad Sci USA 70(5): 1564-1568.
Mechold et al. (1997) Characterization of the Stringent and Relaxed Responses of *Streptococcus equisimilis*. J Bacteriol 179(8): 2658-2667.
Mechold et al., (1996) Functional Analysis of a relA/spoT Gene Homolog from *Streptococcus equisimilis*. J Bacteriol 178(5) 1401-1411.
Mechold et al., (2002) Intramolecular Regulation of the Opposing (p)ppGpp Catalytic Activities of RelSeq, the Rel/Spo Enzyme from *Streptococcus equisimilis*. J Bacteriol 184(11): 2878-2888.

(Continued)

*Primary Examiner* — Jonathan S Lau
(74) *Attorney, Agent, or Firm* — Winston & Strawn LLP

(57) ABSTRACT

Rel proteins as a novel therapeutic agent for treating bacterial threats. More specifically, a novel class of compounds of Formula (I) as disclosed herein which possess antibacterial activity and which inhibit RelA, RelSeq or RelSpo synthetic activity or bacterial spore formation. Also, pharmaceutical compositions of such compounds and a method of combating bacteria, or treating bacterial infections, by administering to a subject in need thereof such compounds or pharmaceutical compositions.

25 Claims, 6 Drawing Sheets

(56) References Cited

OTHER PUBLICATIONS

Metzger et al., (1988) The Nucleotide Sequence and Characterization of the relA gene of *Escherichia coli*. J Biol Chem 263(30): 15699-15704.

Metzger et al., (1989) Protein Sequences Encoded by the relA and the spoT Genes of *Escherichia coli* are Interrelated. J Biol Chem 264(16): 9122-9125.

Mittenhuber (2001) Comparative Genomics and Evolution of Genes Encoding Bacterial (p)ppGpp Synthetases/Hydrolases (the Rel, RelA and SpoT Proteins). J Mol Microbiol Biotechnol 3(4): 585-600.

Murugesan et al., (1985) Analysis of Products Formed during Bleomycin-Mediated DNA Degradation. Biochemistry 24(21): 5735-5744.

Pedersen et al. (1977) Analysis of the relA Gene Product of *Escherichia coli*. Eur J Biochem 76(1): 91-97.

Rodionov et al., (1995) Direct Correlation between Overproduction of Guanosine 3',5'-Bispyrophosphate (ppGpp) and Penicillin Tolerance in *Escherichia coli*. J Bacteriol 177(15): 4224-4229.

Seyfzadeh et al., (1993) spoT-dependent accumulation of guanosine tetraphosphate in response to fatty acid starvation in *Escherichia coli*. Proc Natl Acad Sci USA 90(23): 11004-11008.

Takahashi et al., (2004) Identification of the bacterial alarmone guanosine 5'-diphosphate 3'-diphosphate (ppGpp) in plants. Proc Natl Acad Sci USA 101(12): 4320-4324.

van der Biezen et al., (2000) Arabidopsis RelA/SpoT homologs implicate (p)ppGpp in plant signaling. Proc Natl Acad Sci USA 97(7): 3747-3752.

Wendrich et al., (1997) Cloning and characterization of a relA/spoT homologue from *Bacillus subtilis*. Mol Microbiol 26(1): 65-79.

Wexselblatt et al., (2010) ppGpp analogues inhibit synthetase activity of Rel proteins from Gram-negative and Gram-positive bacteria. Bioorg Med Chem 18(12): 4485-4497.

Xiao et al., (1991) Residual Guanosine 3',5'-Bispyrophosphate Synthetic Activity of relA Null Mutants can be Eliminated by spoT Null Mutations. J Biol Chem 266(9): 5980-5990.

\* cited by examiner

□ %SPORULATIVE CELLS

%INHIBITION OF SPORE FORMATION

▨ 1.8 mM
◩ A 0.9 mM
◪ 2 0.45 mM
◩ 1.8 mM in
  VEGETATIVE
□ 022 mM

AFTER ADDITION OF DIFFERENT CONCENTRATIONS A2:

COMPOUNDS FOR TREATING BACTERIAL INFECTIONS

FIELD OF THE INVENTION

The present invention generally relates to Rel proteins as a novel therapeutic target for treating bacterial threats and more specifically to a novel class of 2'-deoxyguanosine analogs, which possess anti-bacterial activity, to pharmaceutical compositions comprising such compounds, and to methods of use thereof for combating bacteria and treating bacterial infections.

BACKGROUND IN THE INVENTION

Bacteria cells present an outstanding ability to rapidly react to various changes in their growth environment. The number of useful antibiotic agents is decreasing fast. Thus, there is an urgency for finding alternative ways to deal with the crisis.

The natural environment of bacteria is often characterized by changes in nutrient availability. When bacterial cells are deprived of an amino acid or carbon source, changes in many cellular processes occur. Immediately after sensing the inception of amino acid starvation, bacteria respond pleiotropically with the stringent response, which was initially described for *Escherichia coli* in 1961. The first observed feature of the stringent response was the intracellular accumulation of two unusual phosphorylated derivatives of GTP and GDP (collectively named (p) ppGpp), within a few seconds after amino acid starvation (Cashel and Gallant, 1969; Cashel et al., 1969; Cashel et al. 1970). Other features of the stringent response include inhibition of rRNA and tRNA synthesis, inhibition of replication initiation and cell division, suppression of the active transport of many metabolites, transcriptional upregulation of genes encoding enzymes involved in amino acid biosynthesis (Cashel, 1996), and induction of the rpoS gene, which encodes the stationary phase sigma factor (Gentry et al., 1993).

In *E. coli*, the mutation causing the relaxed phenotype, which fails to accumulate (p) ppGpp during amino acid starvation, was mapped to the relA gene which encodes an 84 kDa protein, RelA (Metzger et al., 1988). The RelA protein is a ribosome-associated (p) ppGpp synthetase that is activated in response to amino acid starvation. Synthesis of (p) ppGpp has been characterized as a pyrophosphoryl group transfer of the β and γ phosphates from an ATP donor to the ribose 3' hydroxyl of GTP (or GDP) (Cashel, 1996). For this reaction to occur in vitro, purified RelA requires mRNA, functional ribosomes paused during elongation at a 'hungry codon', and uncharged cognate tRNA bound at the acceptor site of that hungry codon (Cashel, 1996). In cell extracts, RelA is found associated to only a small fraction of the ribosomes (about 1%) (Pedersen and Kjeldgaard, 1977). RelA is thus a ribosome-dependent enzyme that senses environmental amino acid levels by monitoring the amount of uncharged tRNA present in the cell, and accordingly synthesizes the intracellular second-messenger, (p) ppGpp (Haseltine, 1973; Metzger et al., 1988).

In addition to RelA, a second gene product, SpoT, is involved in (p) ppGpp metabolism in *E. coli*. SpoT is a cytosolic protein that functions as a (p) ppGpp synthetase upon carbon or fatty acid limitation (Gentry and Cashel, 1995; Metzger et al., 1989; Seyfzadeh et al., 1993). Equally important, SpoT also acts as a ribosome-independent (p) ppGpp hydrolase that degrades the (p) ppGpp back to GDP(GTP) and pyrophosphate, thus catalyzing a reaction opposing the synthesis of (p) ppGpp from GDP(GTP) and ATP (Metzger et al., 1989). Residual (p) ppGpp synthesis found in a ΔrelA mutant (relA1) is abolished in a ΔrelAΔspoT ("double null") mutant (Xiao et al., 1991). Cells with this double deletion show a complex phenotype, such as loss of ability to grow on amino acid-free minimal medium, morphological alterations and more (Xiao et al., 1991).

It has been found that in several Gram-positive bacteria, only one relA/spoT paralog exists which is capable of carrying out both the (p) ppGpp-synthetase and (p) ppGpp-hydrolase functions (Mechold et al., 1996; Mechold and Malke, 1997; Mittenhuber, 2001; Wendrich and Marahiel, 1997). Deletion of this one gene in gram-positive bacteria creates a phenotype resembling that of the 'double null' *E. coli* cells (Wendrich and Marahiel, 1997). This bifunctional gene product was even found to be essential in the highly pathogenic *Staphyloccous aureus* (Gentry et al., 2000). The gram-negative *Myxococcus xanthus* has both relA and spoT analogs, which appear to be involved in fruiting-body development and spore formation in response to starvation (Harris et al., 1998). Rel/Spo genes are absent in Archaea, in agreement with the transcriptional system being closer to that of eukaryotes, but they are again found in the genome of plants, e.g. *Arabidopsis thaliana*, where they play a role in activating a (p) ppGpp-mediated stress response (van der Biezen et al., 2000; Givens et al., 2004; Takahashi et al., 2004).

The crystal structure of the N-terminal domain (NTD) of Rel/Spo from *Streptococcus equisimilis* (Relseq) reveals two enzyme conformations. This domain has two sub-domains, each with a catalytic site, one responsible for the synthesis of (p) ppGpp, the other for its hydrolysis. The X-ray structure of the NTD also revealed the binding sites for two guanosine nucleotides.

RelA was found to be involved in the virulence, biofilm formation and survival of many bacteria species. Because RelA and its homologues are completely absent in mammals, new antibacterial compounds could be designed based on the known X-ray structure of the NTD of Relseq.

At the onset of sporulation, *B. subtilis* replicates its chromosome and remodels the daughter chromosomes into an elongated axial filament structure, which results in polar septum formation that divides the developing cell into two distinct cells with very different fates, forespore and mother cell. The forespore ultimately becomes the spore, whereas the mother cell nurtures the developing spore until it is discarded by lysis once morphogenesis is complete (Errington et al.). CodY, a highly conserved protein in gram-positive bacteria, regulates the expression of many *Bacillus subtilis* genes that are induced as cells make the transition from rapid exponential growth to stationary phase and sporulation. This transition has been associated with a transient drop in the intracellular pool of GTP.

The stringent response appears to participate in inactivation of CodY in two indirect ways. First, synthesis of (p) ppGpp is at the expense of GTP. Second, Freese et al. showed that (p) ppGpp inhibits IMP dehydrogenase, the first enzyme of the GMP synthesis pathway. Both effects of the stringent response cause a reduction in the GTP pool. Inhibition of ppGpp synthesis may inhibit the drop in GTP level, and consequently CodY would not be inactivated, leading to the inhibition of sporulation.

The applicants of the present invention have previous reported in the use of ppGpp analogues that inhibit the synthetase activity of Rel proteins from both Gram positive and Gram negative bacteria (Wexselblatt et al., WO 2009/116044). The notion is to avoid ppGpp synthesis by inhibiting Rel proteins from both Gram positive and Gram negative bacteria. ppGpp is responsible for penicillin tolerance (Rodionov et al.), and plays an important role in the stringent response as described above. It is hypothesized that by inhibiting this mechanism bacteria will be less tolerant and more susceptible to antibiotic treatment.

There is an ongoing and unmet need in the art to identify new compounds acting as anti-bacterial agents. In addition, there is a need to combat the growing problem of bacterial resistance to anti-bacterial agents.

SUMMARY OF THE INVENTION

The present invention is based on the discovery of a novel class of 2'-guanosine analogs which display activity against a wide range of bacteria. The main difference between these compounds and the previously reported ones resides on the replacement of the highly negatively charged moieties by less polar substituents linked to the sugar ring by either phosphate and/or carbamate linkage. These compounds present higher inhibition than the previously reported. They were shown in vitro to inhibit RelA (*E. Coli*), Relseq (N-terminal domain of Rel/Spo from *S. Equisimilis*) and Rel/Spo (*D. Radiodurance*) synthetic activity as well as spore formation and in vivo inhibition of *B. subtilis* bacteria. The present invention also relates to pharmaceutical compositions comprising such compounds, and to methods of use thereof for combating bacteria and treating bacterial infections.

The present invention relates to Rel proteins as a novel therapeutic target for treating bacterial threats. Without wishing to be bound by any particular mechanism or theory, it is contemplated that, by inhibiting Rel protein (e.g., RelA, Relseq and/or Rel/Spo) synthetic activity, bacteria are prevented from sensing the lack of amino acids in their habitat. This will result in the bacteria not reacting to the changes in their environment, which will ultimately lead to their starvation and death. This mechanism differs from other, frequently used antibacterial compounds in the way that it does not cause selective pressure on the bacteria and therefore will not lead the bacteria to look for alternative pathways to survive.

The present invention concerns compounds denoted by the following formulae as well as by the formulae of particular compounds exemplified herein as non-limiting embodiments.

In one embodiment, the compounds are represented by formula (I), as described herein.

(I)

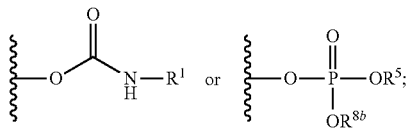

wherein:
X is

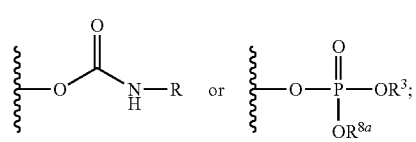

Y is

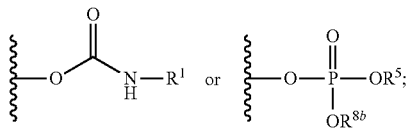

R and $R^1$ are each independently selected from the group consisting of:

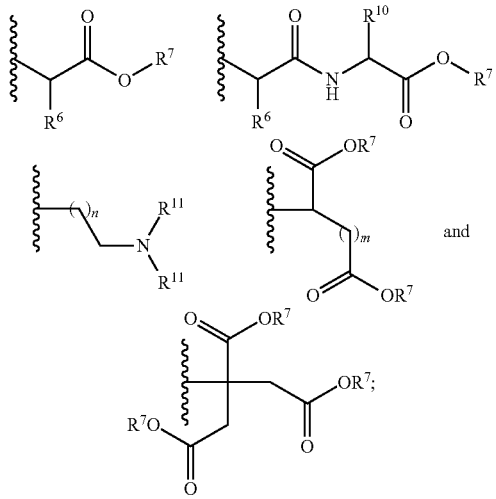

$R^2$ is H or

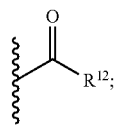

$R^3$ and $R^5$ are each independently H or a moiety selected from the group consisting of:

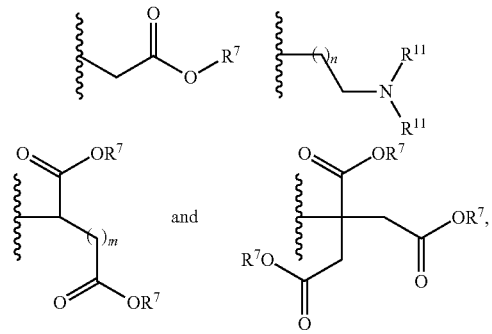

with the proviso that at least one of $R^3$ and $R^5$ is other than H;
$R^7$, $R^{8a}$, $R^{8b}$, $R^9$, $R^{11}$ and $R^{12}$ are each independently H, a $C_1$-$C_6$ alkyl, a $C_1$-$C_6$ alkylaryl, or an aryl;
$R^6$ and $R^{10}$ are each independently a side chain of a natural or unnatural amino acid;
n is 1, 2, 3, 4, 5 or 6; and
m is 1 or 2;

including salts, hydrates, solvates, polymorphs, optical isomers, geometrical isomers, enantiomers, diastereomers, complexes and mixtures thereof.

Non-limiting examples of the compounds of formula (I) include compounds of formulae, A, B, C and D:

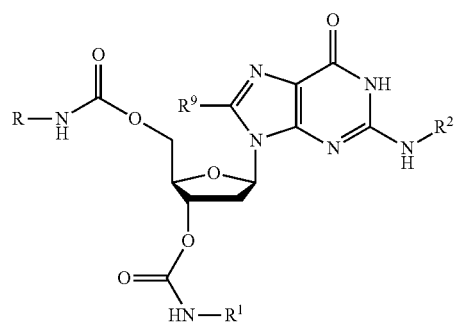

A

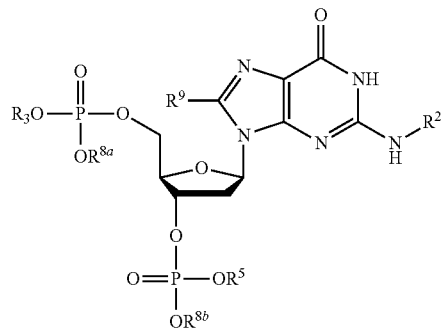

B

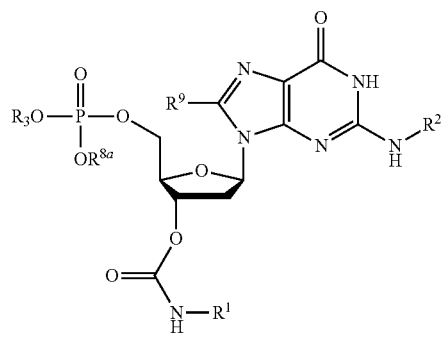

C

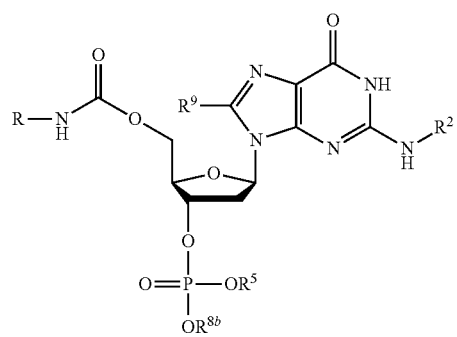

D

In one embodiment, the compound is a compound of Formula A, for example a compound selected from the group consisting of any of formulae A1, A2 and A3 as depicted below.

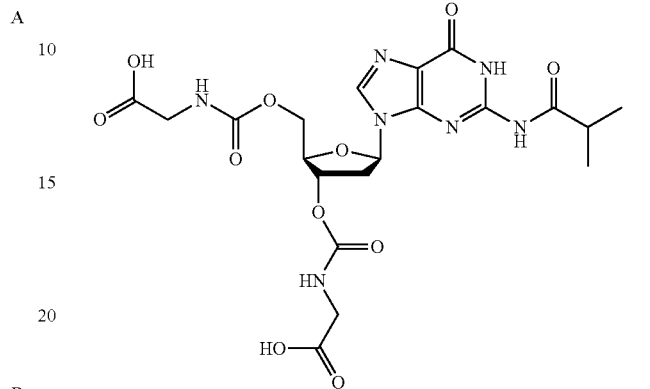

A1

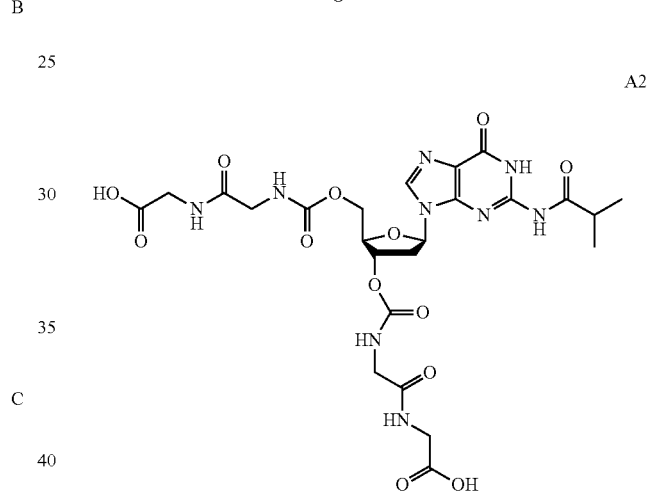

A2

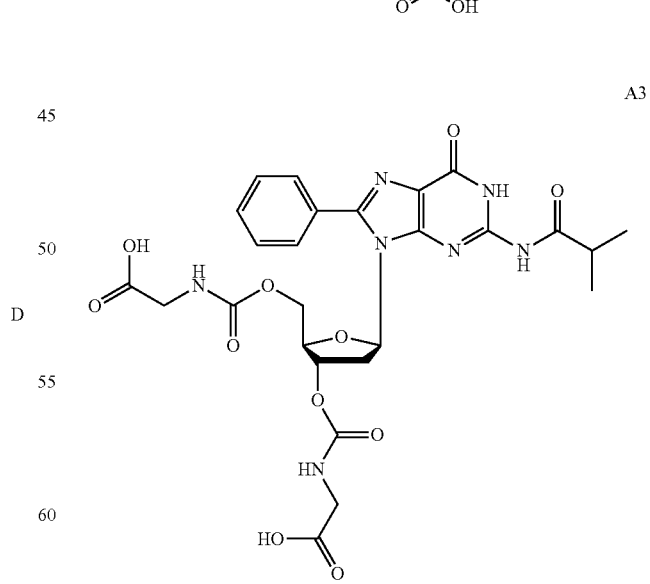

A3

In another embodiment, the compound is a compound of Formula B, for example a compound selected from the group consisting of any of formulae B1, B2 and B3.

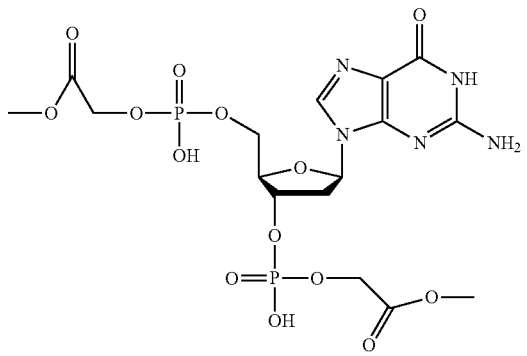

B1

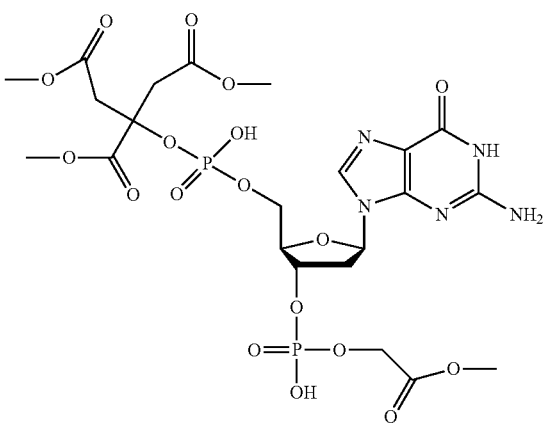

B2

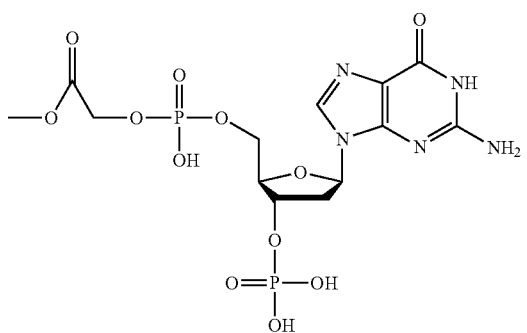

B3

In another embodiment, the compound is a compound of Group C, for example a compound represented by the structure of formula C1:

C1

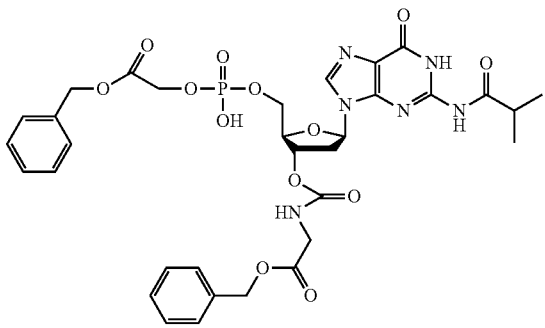

The above compounds, for example compounds from groups B, C and D can be present as isomers, for example, when $R^{8a}$ and/or $R^{8b}$ is methyl. In such a case both isomers separately and as a racemic mix are encompassed by the present invention.

In another aspect, the present invention further relates to a process for preparing the compounds of the present invention of Group A-D, for example compounds of formulae A1, A2, A3, B1, B2, B3 and C1 as described herein.

In another aspect, the present invention is based on the finding and realization that compounds of formula (I), for example Groups A-D as described above, are active as antibacterial agents. Therefore, in another embodiment, the present invention encompasses a pharmaceutical composition comprising a pharmaceutically acceptable carrier or excipient and as an active ingredient a therapeutically effective amount of a compound of formula (I) or of any one of Groups A-D for example compounds of formulae A1, A2, A3, B1, B2, B3 and C1 as described herein, or complexes of the aforementioned compounds with negative charge neutralizing agents. Preferably, the above compositions are anti-bacterial compositions.

In another aspect, the present invention concerns complexes of the compounds of the present invention with "negative charge neutralizing agents"—i.e., agents that when in association with the compounds of formula (I) or compounds of Groups A-D results in either a neutral or a positively charged complex that can easily penetrate through the bacterial membrane. Non-limiting examples of such agents include polyamines, esterifying agents, phosphoramidating agents, and phosphoboronating agents.

In another aspect, the present invention relates to a method of combating bacteria, or treating bacterial infections, comprising the step of administering to a subject in need thereof a compound of formula (I) or a compound of any of Groups A-D as described herein, or a pharmaceutical composition comprising such compound. In another aspect, the method comprises administering a pharmaceutical composition comprising a compound according to formulae A1, A2, A3, B1, B2, B3 or C1 as described herein.

In another aspect, the present invention relates to a method of combating bacteria, comprising the step of contacting the bacteria with a compound of formula (I) or a compound of any of Groups A-D as described herein, or a composition comprising such compound. In another aspect, the method comprises administering a composition comprising a compound according to formula A1, A2, A3, B1, B2, B3 or C1 as described herein.

In another aspect the present invention relates to the use of a compound of formula (I) or a compound any of Groups A-D as described herein, or a pharmaceutical composition comprising such compound, for the manufacture of a medicament for combating bacteria or treating bacterial infections. In another aspect the pharmaceutical composition comprises a compound of formula A1, A2, A3, B1, B2, B3 or C1 as described herein.

In another aspect, the present invention relates to a compound of formula (I) or a compound of any of Groups A-D as described herein, or to a pharmaceutical composition comprising such compound, or to a compound of formula A1, A2, A3, B1, B2, B3 or C1 as described herein, for use in combating bacteria or treating bacterial infections.

The compounds of the invention can be used for inhibition or cession of bacterial growth or as compounds that cause bacterial death, alone or in combination with other antibiotic compounds.

The compounds of the invention may also be used for reduction or prevention of sporulation either alone or in combination with other compounds that are known to affect sporulation. The compounds of the invention may be used as active component of antibacterial or anti sporulation compositions. In one aspect, the antibacterial/anti-sporulation compositions are pharmaceutical compositions for use in human or veterinary medicine for the treatment or prevention of diseases caused or associated with bacterial infection.

In another aspect, the composition may be for non-medicinal use such as for disinfectant purposes, for example for disinfecting surfaces, devices (including medical devices) or non-medicinal compositions (such as cosmetics).

In some embodiments, the bacteria, which are affected by the compounds of the invention with respect to growth, are either gram positive or gram negative, with each possibility representing a separate embodiment of the present invention. An non-limiting example of gram negative bacterial is *E. Coli* from the Enterobacteriaceae family. A non-limiting example of gram positive bacteria is *B. Subtilis* from the *Bacillus* family.

In other embodiments, bacteria which are affected by the compounds of the invention with respect of sporulation are gram positive. A non-limiting example of gram positive bacteria is *B. Subtilis* from the *Bacillus* family.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2: shows the effect of different compounds of the invention on sporulation.

DETAILED DESCRIPTION OF THE INVENTION

Figure 1A:
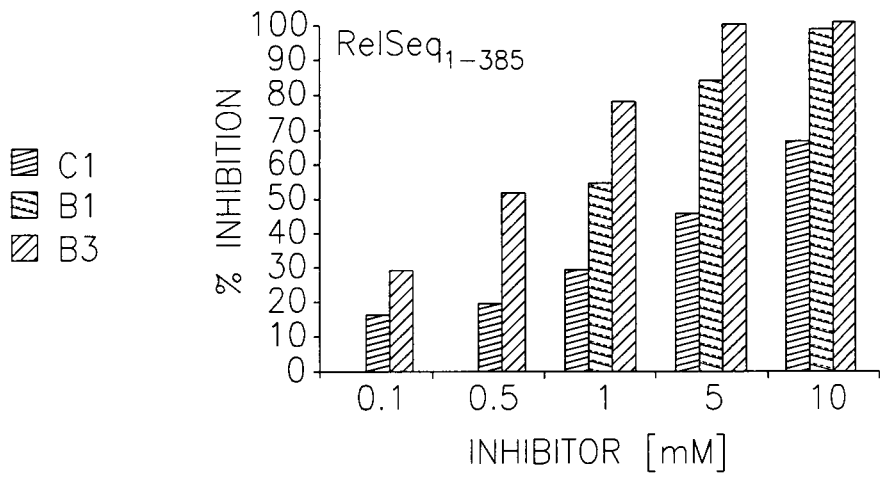
FIG. 1: shows the inhibitory effect of several compounds of the invention in three different systems in vitro: A) the N-terminal domain of Rel/Spo from *E. Equisimilis* ($Rel_{Seq1-385}$), B) RelA from *E. Coli*; and C) Rel/Spo from *D. Radiodurance*. Results are presented as % inhibition vs. compound concentration. Tested compounds are C1, B2 and B3 (FIG. 1A); B1, B2, A1 and B3 (FIG. 1B); and A1 (FIG. 1C).

The present invention is based on the discovery of a novel class of compounds which display activity against a wide range of bacteria. The compounds are guanine nucleoside analogs, which inhibit Rel proteins, e.g., RelA, Relseq and Rel/Spo synthetic activity and possess anti-bacterial activity. The present invention also relates to pharmaceutical compositions comprising such compounds, and to methods of use thereof for combating bacteria and treating bacterial infections in vitro and in vivo, and as disinfectant agents.

Compounds:

In one embodiment, the compounds of the present invention are represented by formula (I), as defined herein.

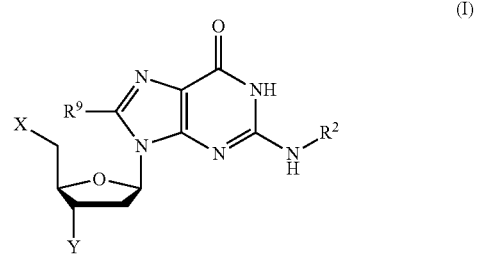

(I)

wherein:

X is

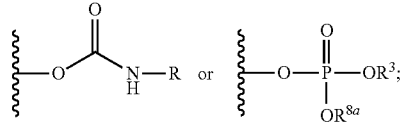

Y is

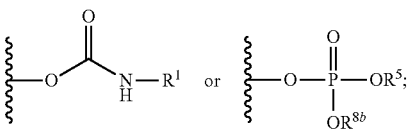

R and $R^1$ are each independently selected from the group consisting of:

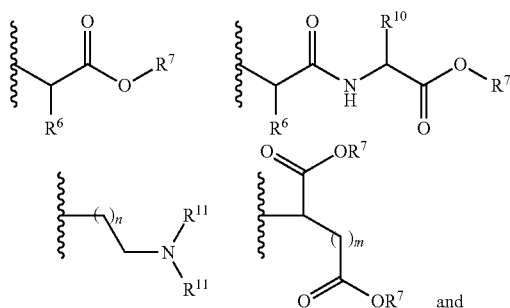

and

-continued

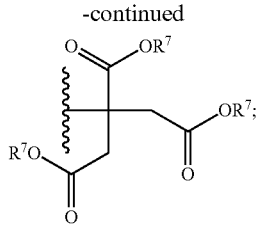

$R^2$ is H or

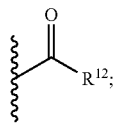

$R^3$ and $R^5$ are each independently H or a moiety selected from the group consisting of:

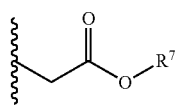 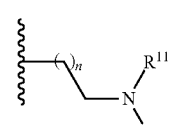

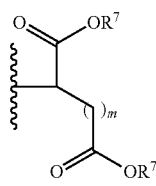 and 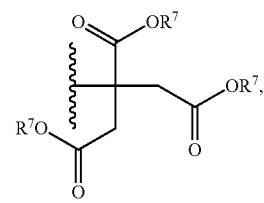

with the proviso that at least one of $R^3$ and $R^5$ is other than H;

$R^7$, $R^{8a}$, $R^{8b}$, $R^9$, $R^{11}$ and $R^{12}$ are each independently H, a $C_1$-$C_6$ alkyl, a $C_1$-$C_6$ alkylaryl, or an aryl;

$R^6$ and $R^{10}$ are each independently a side chain of a natural or unnatural amino acid;

n is 1, 2, 3, 4, 5 or 6; and m is 1 or 2;

including salts, hydrates, solvates, polymorphs, optical isomers, geometrical isomers, enantiomers, diastereomers, complexes and mixtures thereof.

In one embodiment, the present invention relates to a compound of formula (I) wherein R and $R^1$ are each independently selected form (a), (b), (c), (d), and (e):

a) a monocarboxylic acid derivative of formula

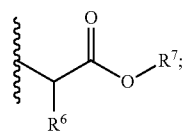

(b) a dicarboxylic acid derivative of formula

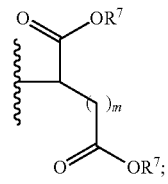

(m = 1)

(c) a tricarboxylic acid derivative of the formula

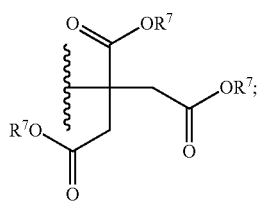

(d) a dipeptide derivative of formula

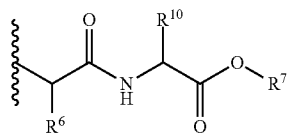

wherein $R^6$ and $R^{10}$ are the same or different and are each independently a side chain of glutamic acid, valine, lysine or glycine; and (e) dimethylamino propyl.

Each possibility represents a separate embodiment of the present invention.

In one embodiment, $R^2$ in formula (I) is selected from:

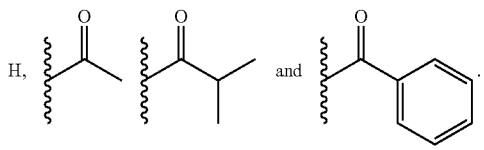

Preferably $R^2$ in formula (I) is H or —CO—CH(CH$_3$)$_2$ (isobutyryl). Each possibility represents a separate embodiment of the present invention.

In one embodiment, the present invention relates to a compound of formula (I) wherein $R^3$ and $R^5$ are each independently selected from the group consisting of:

(a) H;

(b) a monocarboxylic acid derivative of formula

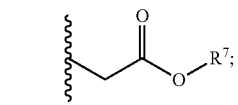

(c) a dicarboxylic acid derivative of formula

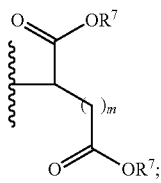

(m = 1)

(d) a tricarboxylic acid derivative of formula

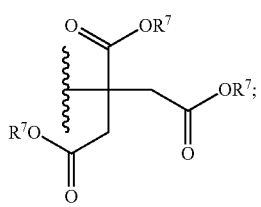

wherein $R^7$ is H, methyl, ethyl or benzyl, and with the proviso that at least one of $R^3$ and $R^5$ is other than H. Each possibility represents a separate embodiment of the present invention.

In another embodiment, $R^{8a}$ and $R^{8b}$ in formula (I) are each independently H or methyl. In another embodiment, $R^7$ is in formula (I) independently at each occurrence H, methyl, ethyl or benzyl. In another embodiment, $R^9$ in formula (I) is H or phenyl. Each possibility represents a separate embodiment of the present invention.

In one embodiment, of formula (I), X is

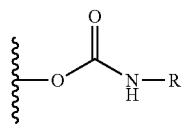

and Y is

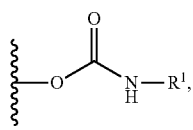

and the compound is represented by the structure of formula A:

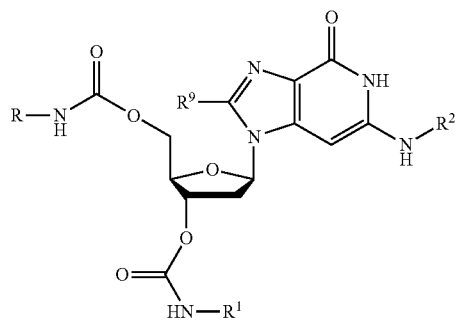

Preferred compounds of formula A are those wherein R and $R^1$ are each independently:

(a) a monocarboxylic acid derivative of formula

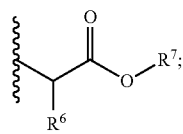

(b) a dicarboxylic acid derivative of formula

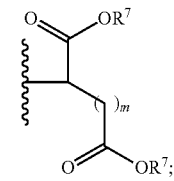

(m = 1)

(c) a tricarboxylic acid derivative of the formula

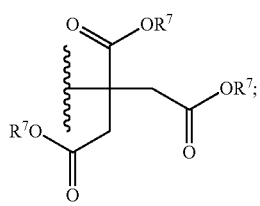

(d) a dipeptide derivative of formula

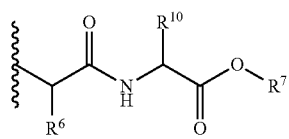

wherein $R^6$ and $R^{10}$ are the same or different and are each independently a side chain of glutamic acid, valine, lysine or glycine; and (e) dimethylamino propyl.

Each possibility represents a separate embodiment of the present invention.

Other preferred compounds of formula A are those wherein R and $R^1$ are each independently

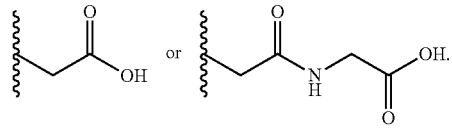

Other preferred compounds of formula A are those wherein $R^2$ is H or —CO—CH(CH$_3$)$_2$.

Other preferred compounds of formula A are those wherein R and $R^1$ are each a monocarboxylic acid derivative of formula

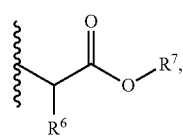

and R² is —CO—CH(CH₃)₂.

Particular and non-limiting examples of compounds of formula A are those represented by the structure of formula A1, A2 or A3:

A1

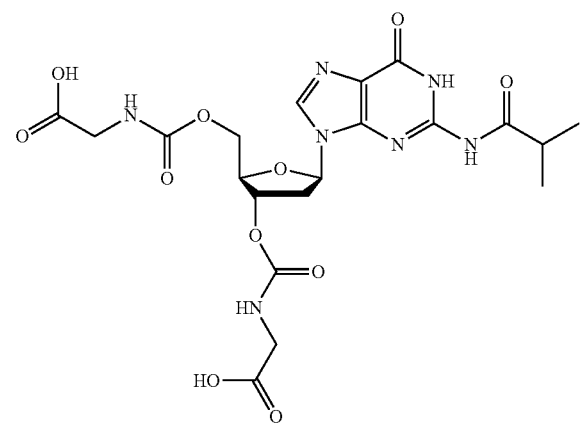

A2

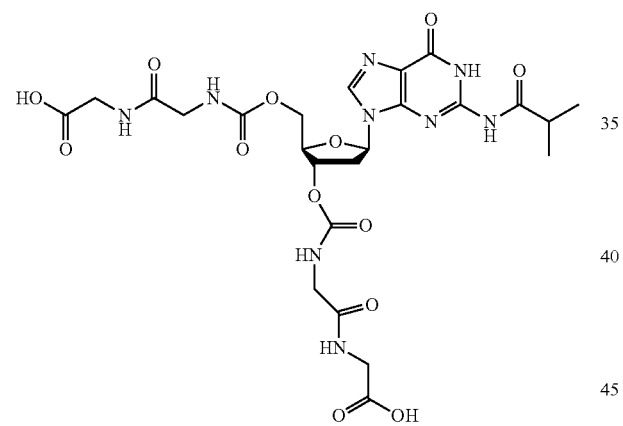

A3

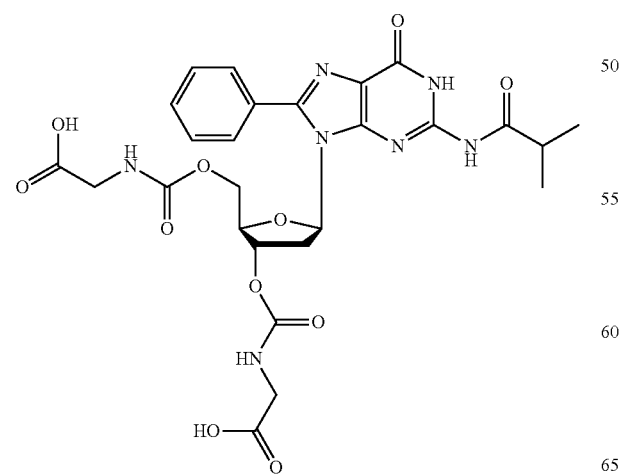

In another embodiment, of formula (I), X is

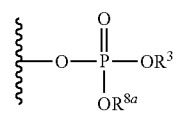

and Y is

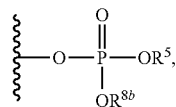

and the compound is represented by the structure of formula B:

B

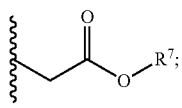

Preferred compounds of formula B are those wherein $R^3$ and $R^5$ are each independently selected from the group consisting of:

(a) H;

(b) a monocarboxylic acid derivative of formula

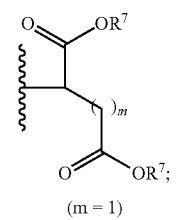

(c) a dicarboxylic acid derivative of formula

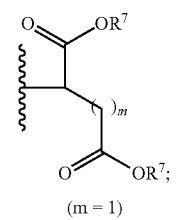

(m = 1)

(d) a tricarboxylic acid derivative of formula

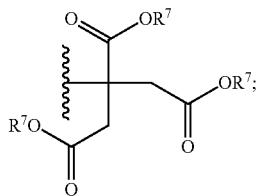

wherein R⁷ is H, methyl, ethyl or benzyl. Each possibility represents a separate embodiment of the present invention.

Other preferred compounds of formula B are those wherein $R^{8a}$ and $R^{8b}$ are each independently H or methyl.

Other preferred compounds of formula B are those wherein $R^2$ is H or —CO—CH(CH$_3$)$_2$.

Other preferred compounds of formula B are those wherein $R^3$ and $R^5$ are each independently (a) a monocarboxylic acid derivative of formula or

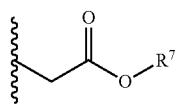

(b) a tricarboxylic acid derivative of formula

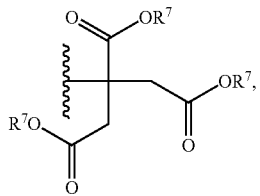

$R^2$, $R^{8a}$ and $R^{8b}$ are each H, and $R^7$ is a methyl group.

Other preferred compounds of formula B are those wherein $R^3$ is a monocarboxylic acid of formula

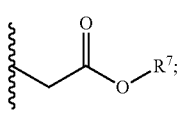

$R^2$, $R^5$, $R^{8a}$ and $R^{8b}$ are each H; and $R^7$ is methyl.

In one embodiment of formula B, $R^3$ is other than H. In another embodiment of formula B, $R^5$ is other than H. In another embodiment of formula B, each of $R^3$ and $R^5$ is other than H. Each possibility represents a separate embodiment of the present invention.

Particular and non-limiting examples of compounds of formula B are those represented by the structure of formula B1, B2 or B3:

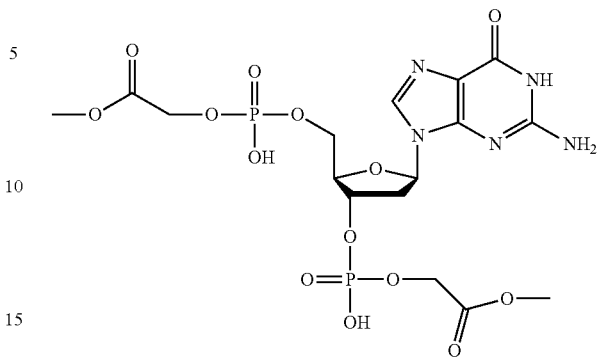

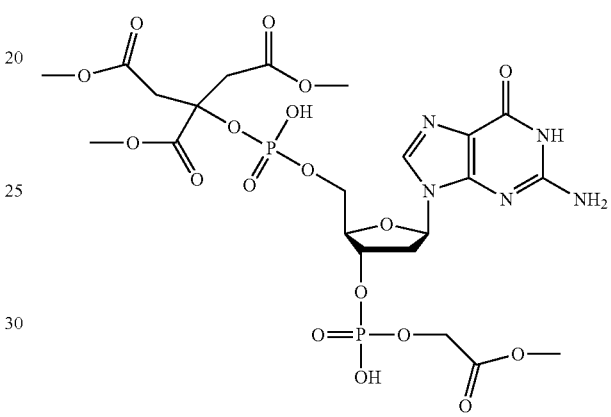

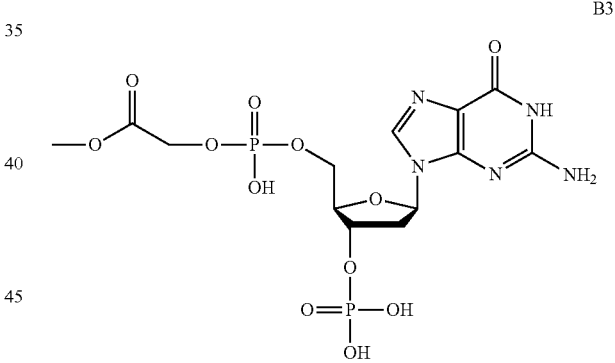

In another embodiment, of formula (I), X is

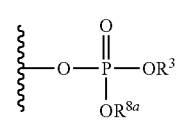

and Y is

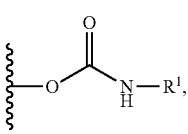

and the compound is represented by the structure of formula C:

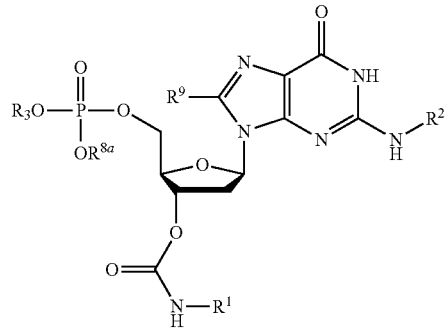

Preferred compounds of formula C are those wherein $R^1$ is selected from the group consisting of:

(a) a monocarboxylic acid derivative of formula

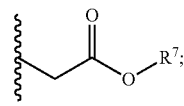

(b) a dicarboxylic acid derivative of formula

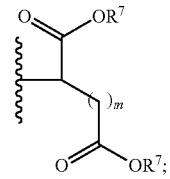

(m = 1)

(c) dimethylamino propyl.

Each possibility represents a separate embodiment of the present invention.

Other preferred compounds of formula C are those wherein $R^3$ is a monocarboxylic acid derivative of formula

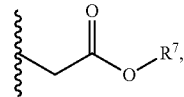

wherein $R^7$ is benzyl.

Other preferred compounds of formula C are those wherein $R^{8a}$ is H or methyl.

Other preferred compounds of formula C are those wherein $R^2$ is H or —CO—CH(CH$_3$)$_2$.

Other preferred compounds of formula C are those wherein $R^1$ and $R^3$ are a monocarboxylic acid derivative of formula

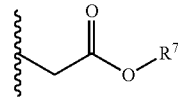

wherein $R^7$ is benzyl, $R^2$ is H or —CO—CH(CH$_3$)$_2$, and $R^{8a}$ is H.

Other preferred compounds of formula C are those wherein $R^3$ is other than H.

A particular and non-limiting example of compounds of formula C is a compound represented by the structure of formula C1:

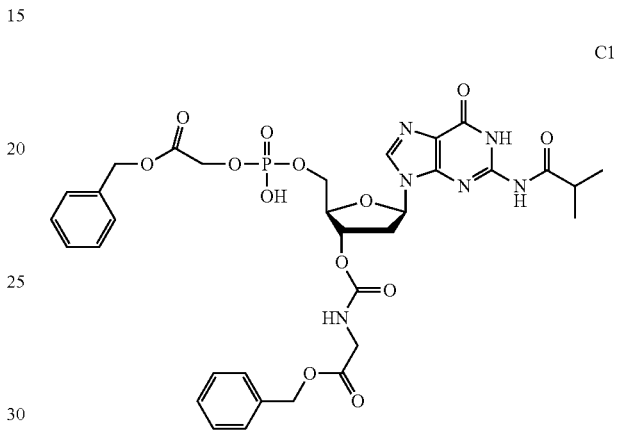

In another embodiment, of formula (I), X is

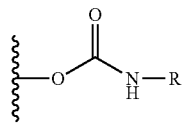

and Y is

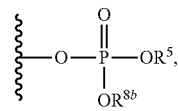

and the compound is represented by the structure of formula D:

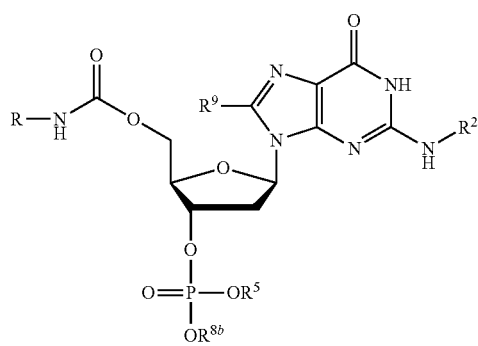

Preferred compounds of formula D are those wherein R is selected from the group consisting of:
(a) a monocarboxylic acid derivative of formula and

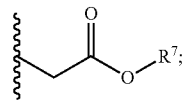

(b) a dicarboxylic acid derivative of formula

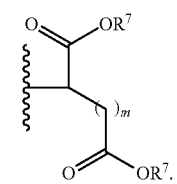

(m = 1)

Other preferred compounds of formula D are those wherein $R^5$ is selected from the group consisting of:
(a) a monocarboxylic acid derivative of formula and

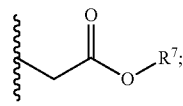

(b) a dicarboxylic acid derivative of formula wherein $R^7$ is benzyl.

(m = 1)

Other preferred compounds of formula D are those wherein $R^{8b}$ is H or methyl. Other preferred compounds of formula D are those wherein $R^2$ is H or —CO—CH(CH$_3$)$_2$. Other preferred compounds of formula D are those wherein $R^5$ is other than H.

Other preferred compounds of the invention include, but are not limited to:
a) Compounds from group A where R and $R^1$ are mono, di and tri carboxylic acids; dipeptides consisting on di-glutamic acid, di-valine and di-lysine or dimethyl amino propyl moiety and $R^2$ is either H or isobutyric substituent.
b) Compounds from group B where $R^3$ and $R^5$ are mono, di and tri carboxylic acids being $R^7$ ethyl, methyl or benzyl, $R^8$ is either methyl or H and $R^2$ is H.
c) Compounds from group C where $R^1$ is mono or di-carboxylic acid or dimethyl amino propyl moiety, $R^3$ is a mono carboxylic acid being $R^7$ benzyl, $R^8$ is either methyl or H and $R^2$ is either H or isobutyric substituent.
d) Compounds from group C where R is mono or di-carboxylic acid, $R^5$ is mono or di-carboxylic acid being $R^7$ benzyl, $R^8$ is either methyl or H and $R^2$ is either H or isobutyric substituent.

Specific compounds of the invention include, but are not limited to:
a) Compound from group A where R and $R^1$ are mono carboxylic acids and $R^2$ is an isobutyric moiety (A1).
b) Compound from group B where $R^3$ and $R^5$ are either mono (B1) or tri (B2) carboxylic acids, $R^8$ is H, $R^2$ is H and $R^7$ is a methyl group.
c) Compound from group B where $R^3$ is mono carboxylic acid, $R^7$ is methyl, $R^8$, $R^2$ and $R^5$ are H (B3).
d) Compound from group D where $R^1$ and $R^3$ are mono carboxylic acids, $R^7$ is a benzyl moiety, $R^2$ is an isobutyric moiety and $R^8$ is H(C1).

In another aspect, the present invention concerns complexes of compounds formula (I) or compounds of Groups A-D with "negative charge neutralizing agents"—i.e., agents that when in association with the compounds of formula (I), or compounds of Groups A-D result in either a neutral or a positively charged complex that can easily penetrate through the bacterial membrane. Non-limiting examples of such agents include polyamines, esterifying agents, phosphoramidating agents, and phosphoboronating agents.

The term "complex" may refer to electrostatic interaction between the charged compounds of the invention and the opposite charge "negative charge neutralizing agents". This term may also refer to covalent binding between the charged compounds of the invention and the opposite charge "negative charge neutralizing agents" preferably by bonds that can be cleaved once inside the bacterial cell.

CHEMICAL DEFINITIONS

The term "$C_1$ to $C_6$ alkyl" or "$C_{1-6}$ alkyl", used herein alone or as part of another group denotes a linear and branched, saturated alkyl group containing 1 to 6 carbon atoms. Examples of saturated alkyl groups include but are not limited to methyl, ethyl, n-propyl, isopropyl, n-butyl, iso-butyl, sec-butyl, tert-butyl, 1-pentyl, 2-pentyl, 3-pentyl. Similarly, the term "$C_1$ to $C_6$ alkylene" or "$C_{1-6}$ alkylene" denotes a bivalent radical of 1 to 6 carbons.

The $C_1$ to $C_6$ alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio, arylthio, or $C_1$ to $C_{10}$ alkylsulfonyl groups. Any substituent can be unsubstituted or further substituted with any one of these aforementioned substituents.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "alkylaryl" as used herein alone or as part of another group denotes an alkyl group as defined herein, attached to an aryl group as defined herein. The alkylaryl group can be unsubstituted or substituted through available carbon atoms with one or more groups defined hereinabove for alkyl.

Several of the compounds of the present invention contain side chains of amino acids. The invention encompasses compounds having side chains of natural and unnatural amino acids, meaning both the naturally occurring amino acids and other unnaturally amino acids including both optically active (D and L) forms as well as racemic derivatives. The naturally occurring amino acids are, e.g., glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. A preferred amino acid is glycine. Another preferred amino acid is glutamic acid. Another preferred amino acid is valine. Another preferred amino acid is lysine. Examples of unnatural α-amino acids include, but are not limited to, α-aminoisobutyric acid, α-aminobutyric acid, γ-aminobutyric acid, citrulline, homocitrulline, homoproline, homoserine, hydroxyproline, norleucine, 4-aminophenylalanine, 4-halo phenyl alanine (e.g., 4-fluoro, bromo, chloro or iodo phenylalanine wherein), 4-nitro phenylalanine, statine, hydroxylysine, kynurenine, 3-(2'-naphthyl)alanine, 3-(1'-naphthyl)alanine, methionine sulfone, (t-butyl)alanine, (t-butyl) glycine, 4-hydroxyphenylglycine, aminoalanine, phenylglycine, vinylalanine, propargyl-glycine, 1,2,4-triazolo-3-alanine, thyronine, 6-hydroxytryptophan, 5-hydroxytryptophan, 3-hydroxykynurenine, 3-aminotyrosine, trifluoromethyl-alanine, 2-thienylalanine, (2-(4-pyridyl)ethyl) cysteine, 3,4-dimethoxy-phenylalanine, 3-(2'-thiazolyl) alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, elastatinal, norleucine, norvaline, alloisoleucine, homoarginine, thioproline, dehydroproline, hydroxyproline, homoproline, α-amino-n-butyric acid, cyclohexylalanine, 2-amino-3-phenylbutyric acid, β-2- and 3-thienylalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-(sulfo)tyrosine, 3-(carboxy)tyrosine, 3-(phospho)tyrosine, the 4-methane sulfonic acid ester of tyrosine, 4-methane phosphonic acid ester of tyrosine, 3,5-diiodotyrosine, 3-nitrotyrosine, ε-alkyl lysine, and δ-alkyl ornithine, Dap (i.e., the side chain is $CH_2NH_2$), dimethyl Dap (i.e., the side chain is $CH_2N(CH_3)_2$), dimethylamino lysine (i.e., the side chain is $(CH_2)_4$—$N(CH_3)_2$), Dab (i.e., the side chain is $CH_2CH_2NH_2$), Abu (i.e., the side chain is $CH_2CH_3$), Apn (i.e., the side chain is $CH_2CH_2CH_3$), and Ahx (i.e., the side chain is $(CH_2)_3$—$CH_3$).

A "OH protecting group" or "hydroxy protecting group" refers to a readily cleavable groups bonded to hydroxyl groups. An example of a hydroxy protecting group is an acyl group (COR wherein R=alkyl, aryl, etc.), such as an acetyl group (OAc). Another example of a hydroxy protecting group is a silyl group, which can be substituted with alkyl (trialkylsilyl), with an aryl (triarylsilyl) or a combination thereof (e.g., dialkylphenylsilyl). A preferred example of a silyl protecting group is trimethylsilyl (TMS) or di-t-butyldimethyl silyl (TBDMS). Other examples of hydroxy protecting groups include, for example, $C_1$-$C_4$ alkyl (e.g., methyl, ethyl, propyl, butyl and the like), —$CH_2Ph$ (benzyl or bzl), allyl (allyl)-CO—($C_1$-$C_6$ alkyl), —$SO_2$—($C_1$-$C_6$ alkyl), —$SO_2$-aryl, —CO—Ar in which Ar is an aryl group as defined above, and —CO—($C_1$-$C_6$ alkyl)Ar (e.g., a carboxybenzyl (Bz) group). Other examples of hydroxy protecting groups include acid sensitive protecting groups such as tetrahydropyranyl (THP), methoxymethyl (MOM), tert-butyldimethylsilyl (TBDMS) and triphenylmethyl (Trityl) and dimethoxy trityl (DMT). Each possibility represents a separate embodiment of the present invention. Other examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, T. W. Greene and P. G. M. Wuts, "Protective Groups in Organic-Synthesis,"2nd ed., John Wiley and Sons, New York, N.Y., 1991, Chapters 2 and 3, or Kocienski, Philip J. Protecting Groups. 3rd Ed. 2005, (2005), 679 pp., each of which is incorporated herein by reference.

As used herein, the term "leaving group" (LG) refers to any labile group. Suitable leaving groups are, for example, halogen, e.g. Cl, Br or I, or an organosulfonyloxy radical ($OSO_2R'$), for example, mesyloxy, tosyloxy, trifloxy and the like. Another example of a leaving group is a moiety of formula OR" wherein R" can be any hydroxy protecting group as defined above. Other examples of leaving groups are aromatic amines such as imidazole. Each possibility represents a separate embodiment of the present invention.

Several compounds of the present invention, e.g., compounds from groups B, C and D can be present as isomers. In such a case both isomers separately and as a racemic mix are encompassed by the present invention. All stereoisomers, optical and geometrical isomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. Compounds comprising amino acid residues include residues of D-amino acids, L-amino acids, or racemic derivatives of amino acids.

One or more of the compounds of the invention, may be present as a salt. The term "salt" encompasses both basic and acid addition salts, and include salts formed with organic and inorganic anions and cations. Furthermore, the term includes salts that form by standard acid-base reactions of basic groups and organic or inorganic acids. Such acids include hydrochloric, hydrofluoric, hydrobromic, trifluoroacetic, sulfuric, phosphoric, acetic, succinic, citric, lactic, maleic, fumaric, cholic, pamoic, mucic, D-camphoric, phthalic, tartaric, salicyclic, methanesulfonic, benzenesulfonic, p-toluenesulfonic, sorbic, picric, benzoic, cinnamic, and like acids.

The term "organic or inorganic cation" refers to counterions for an acid. The counter-ions can be chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylene diammonium, and like cations. See, for example, "Pharmaceutical Salts," Berge et al., *J. Pharm. Sci.*, 66:1-19 (1977), which is incorporated herein by reference. Furthermore, any zwitterionic form of the instant compounds formed by a carboxylic acid and an amino group are also contemplated.

The present invention also includes solvates of the compounds of the present invention and salts thereof "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR spectra, melting point, and the like.

Therapeutic Uses:

As contemplated herein, the present invention is based on the finding that compounds of formula (I) or compounds of groups A-D as described above are active as antibacterial agents. It is further contemplated that the compounds of the present invention act by inhibiting the synthetic pathways of Rel proteins such as RelA and/or Relseq and/or Rel/Spo. It is apparent to a person of skill in the art that the purported mechanism by which the compounds of the present invention act does not limit the broad scope of the invention.

The antibacterial compositions of the invention may be used for medicinal purposes and in such a case the composition is a pharmaceutical composition for the treatment of bacterial infections.

Thus, another aspect, the present invention relates to a method of combating bacteria, or treating bacterial infections, comprising the step of administering to a subject in need thereof a compound of formula (I) or a compound of any of Groups A-D as described herein, or a pharmaceutical composition comprising such compound. In another embodiment, the method comprises administering a pharmaceutical composition comprising an effective amount of any a complex of a compound of the present invention with a negative charge neutralizing agent.

In another aspect, the present invention relates to the use of a compound of formula (I) or a compound any of Groups A-D as described herein, or a pharmaceutical composition comprising such compound, or a complex of such compound with a negative charge neutralizing agent, for the manufacture of a medicament for combating bacteria or treating bacterial infections.

In another aspect, the present invention relates to a compound of formula (I) or a compound of any of Groups A-D as described herein, or to a pharmaceutical composition comprising such compound, or a complex of such compound with a negative charge neutralizing agent, for use in combating bacteria or treating bacterial infections.

The anti bacterial composition may also be used for disinfecting purposes for example of surfaces, devices (including medical devices), cultures of eukaryotic cells or tissue, water pipes and water filters, food and agricultural products. The present invention further concerns a method for combating bacteria the method comprising contacting the bacteria with an effective amount of compound of formula (I) or a compound of any of Groups A-D as described herein, or with a complex of these compounds with a negative charge neutralizing agent, or a pharmaceutical composition comprising such compound. The contact may be ex vivo on a surface, on a device, in cell/tissue culture dish, in food, water, agricultural product as described above. Alternatively the contact may be in the body of a human or non human subject.

The term "anti-bacterial" may refer to one or more of the following effects: killing the bacteria (bacteriocide), causing halt of growth of bacteria (bacteriostatic), prevention of bacterial infection, prevention of bio-film formation and disintegration of a formed biofilm, and decrease in bacterial virulence.

Examples of bacterial strain that can be treated/disinfected by the composition of the invention (both as a disinfecting composition and as a pharmaceutical composition) are all gram negative and gram positive bacteria and in particular pathogenic gram negative and gram positive bacteria.

The term "combating bacteria" or "treating bacterial infection" may refer to one of the following: decrease in the number of bacteria, killing or eliminating the bacteria, inhibition of bacterial growth (stasis), inhibition of bacterial infestation, inhibition of biofilm formation, disintegration of existing biofilm, or decrease in bacterial virulence.

The methods of the invention both ex-vivo and in the body of the subject may further comprise co administration of at least one additional anti-bacterial agent such as state of the art antibiotics.

The compounds of the invention can be used for inhibition or cession of bacterial growth or as compounds that cause bacterial death, alone or in combination with other antibiotic compounds. Suitable antibiotic agents to be used in combination with the compounds of the invention include, but are not limited to penicillins, cephalosporins, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and others. Particular examples are beta-lactam antibiotics such as amoxycillin, ampicillin, azlocillin, aztreonam, cefazolin, ceftazidime, cefuroxime, cefaclor, cefotaxime, ceftriaxone, ceftizaxime, cefoperazone, cefepime, cefpirome, cefinenoxime, cefoxitin, cefixime, cefpodoxime, ceftibuten, cefprozil, cephalexin, cephaloridine, ertapenem, imipenem, mecillinam, meropenem, methicillin, moxolactam, oxacillin, panipenem, penicillin G or V, piperacillin and ticarcillin.

The compounds of the invention may also be used for reduction or prevention of sporulation either alone or in combination with other compounds that are known to affect sporulation, examples of which include, but are not limited to antibiotics such as Chloramphenicol, Streotpmycin and Kanamycin.

Pharmaceutical Compositions

In another aspect, the present invention is based on the finding and realization that the compounds of the invention (i.e., compounds of formula (I) or compounds of Groups A-D), can be active as antibacterial agents. Therefore, in another embodiment, the present invention concerns an pharmaceutical composition comprising a pharmaceutically acceptable carrier or excipient and as an active ingredient a therapeutically effective amount of a compound of formula (I) or a compound any one of Groups A-D, for example compounds of formulae A1, A2, A3, B1, B2, B3 or C1 as described hereinabove, or complexes of the aforementioned compounds with negative charge neutralizing agents as described above. Preferably the above compositions are antibacterial compositions.

In an alternative embodiment, the compound of formula (I) may be a compound of Group A, for example a compound selected from the group consisting of any of formulae A1, A2 and A3 as depicted herein.

In an alternative embodiment, the compound of formula (I) may be a compound of Group B, for example a compound selected from the group consisting of any of formulae B1, B2 and B3 as depicted herein.

In an alternative embodiment, the compound of formula (I) may be a compound of Group C, for example a compound represented by the structure of formula C1 as depicted herein.

In an alternative embodiment, the compound of formula (I) may be a compound of Group D.

The pharmaceutical compositions of the present invention can be formulated for administration by a variety of routes including oral, vaginal, rectal, ocular, transdermal, parenteral (subcutaneous, intraperitoneal, intravenous, intraarterial, transdermal and intramuscular), mucosal, topical, intranasal, via a suppository or by inhalation. Such compositions are prepared in a manner well known in the pharmaceutical art and comprise as an active ingredient at least one compound of the present invention as described herein, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In another embodiment, the compounds of the present invention can be added to a person's diet by mixing them with food or drink.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

The amount of a compound of the invention that will be effective in the treatment of a particular anti-bacterial infection, will depend on the nature of the infection, and can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each patient's circumstances. A preferred dosage will be within the range of 0.01-1000 mg/kg of body weight, more preferably, 0.1 mg/kg to 100 mg/kg and even more preferably 1 mg/kg to 10 mg/kg. Effective doses may be extrapolated from dose-response curves derived from in vitro or animal model test bioassays or systems.

Synthesis:

The Compounds of the present invention may be synthesized in any manner known to a person of skill in the art as further exemplified in the Experimental Section in several non-limiting embodiments.

In general, compounds of formula A may be synthesized in accordance with the process set forth in Scheme 1:

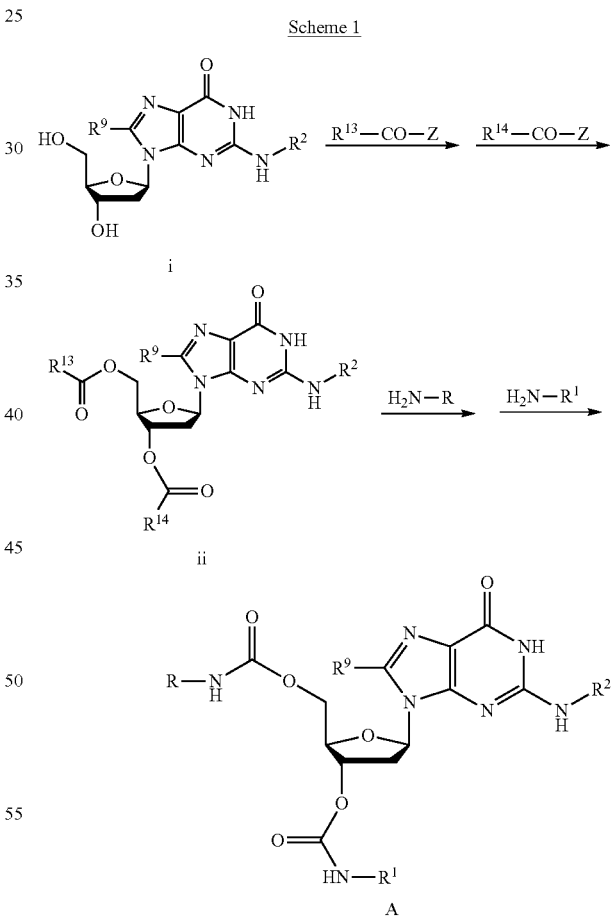

In Scheme 1, a precursor of formula (I) is activated with a compound of formula $R^{13}$—CO—Z or $R^{14}$—CO—Z wherein Z is a leaving group to form an activated derivative of formula (ii), which is reacted with the appropriate amine compound of formula $H_2N$—R and $H_2N$—R' wherein R and $R^1$ are as defined above to form a carbamate and thereby generate the product of formula A. It is apparent to a person of skill in the art that the hydroxyl groups of compound (i) may be selectively protected with any hydroxyl protecting groups, and that the hydroxyl activating groups and the amines can be selectively introduced to their respective positions in any order, with and without initial protection of the hydroxyl groups of formula (i).

In general, compounds of formula B may be synthesized in accordance with the process set forth in Scheme 2:

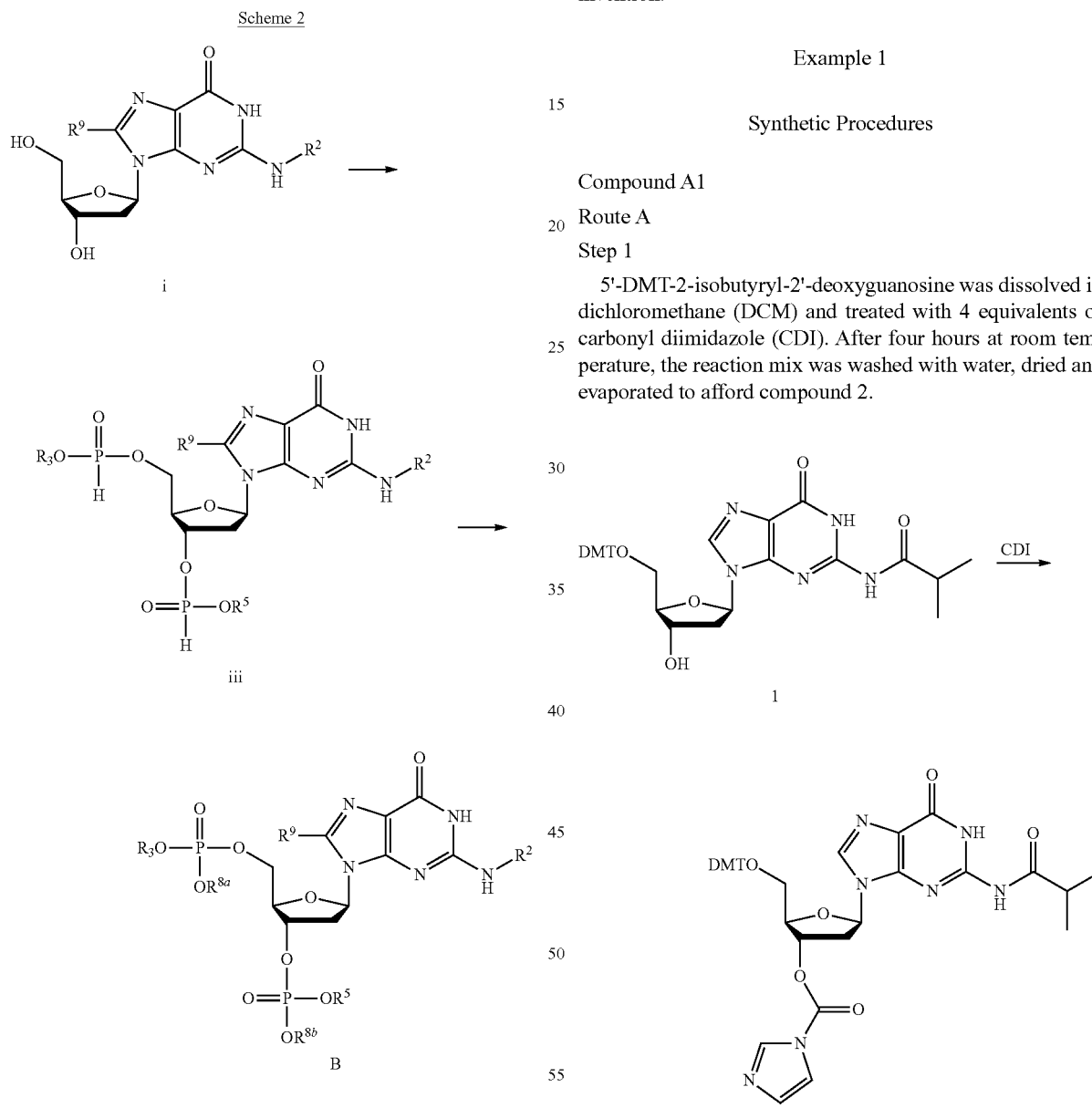

In Scheme 2, a precursor of formula (I) is reacted with a phosphite derivative to generate a compound of formula (iii) which is then oxidized (e.g., with $I_2$ or any other oxidizing agent) to generate the corresponding phosphate ($R^{8a}$ and $R^{8b}$=H), which can then be converted to a compound of formula B by introduction of the groups $R^{8a}$ and $R^{8b}$.

Compounds of formula (C) and (D), which contain one carbamate group and one phosphate group can be prepared in a similar manner by introduction of the carbamate group as exemplified in Scheme 1, and the phosphate group as exemplified in Scheme 2, in any order.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

Synthetic Procedures

Compound A1

Route A

Step 1

5'-DMT-2-isobutyryl-2'-deoxyguanosine was dissolved in dichloromethane (DCM) and treated with 4 equivalents of carbonyl diimidazole (CDI). After four hours at room temperature, the reaction mix was washed with water, dried and evaporated to afford compound 2.

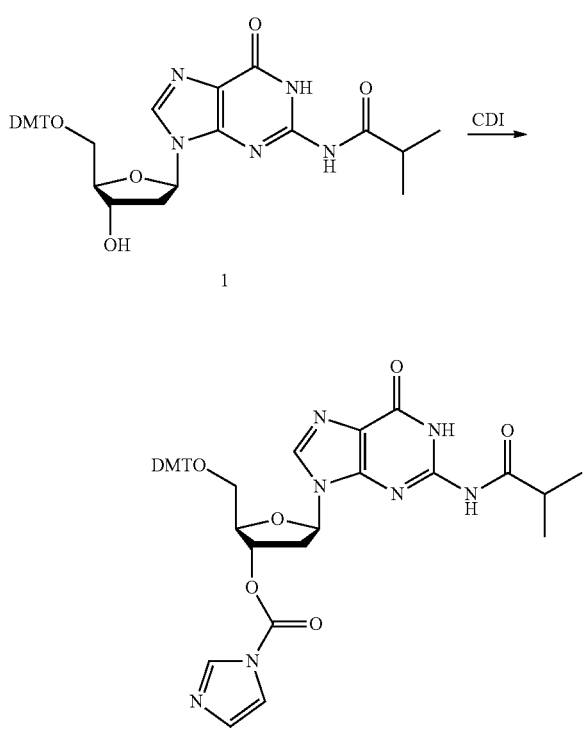

Step 2

Compound 2 was dissolved in DCM and treated with glycine benzyl ester and diisopropyl ethyl amine (DIEA). The reaction was stirred for 20 hours, washed with water and a solution of citric acid. The organic phase was dried and evaporated. The crude was purified by liquid chromatography.

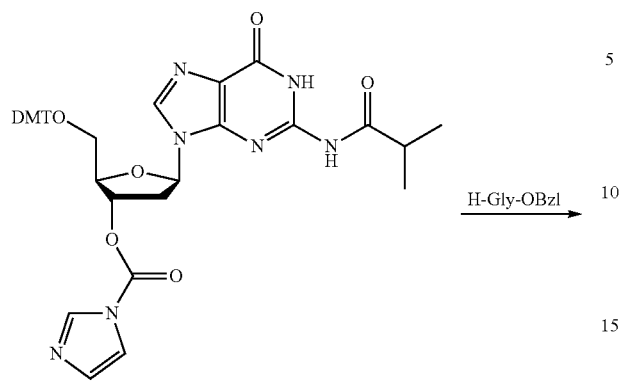
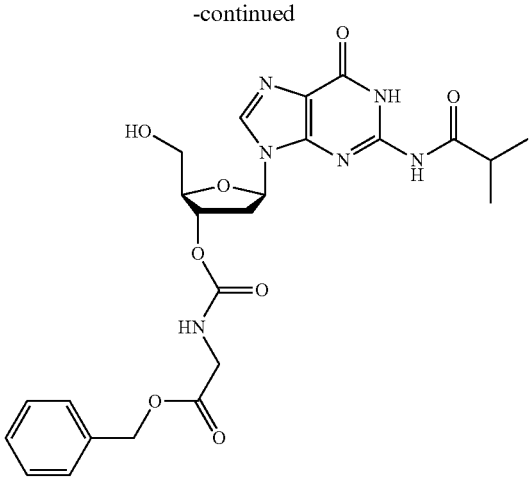
Step 4
Compound 4 was dissolved in DCM and treated with 4 equivalents of CDI. After four hours at room temperature the reaction mixture was washed with water, dried and evaporated to obtain compound 5.
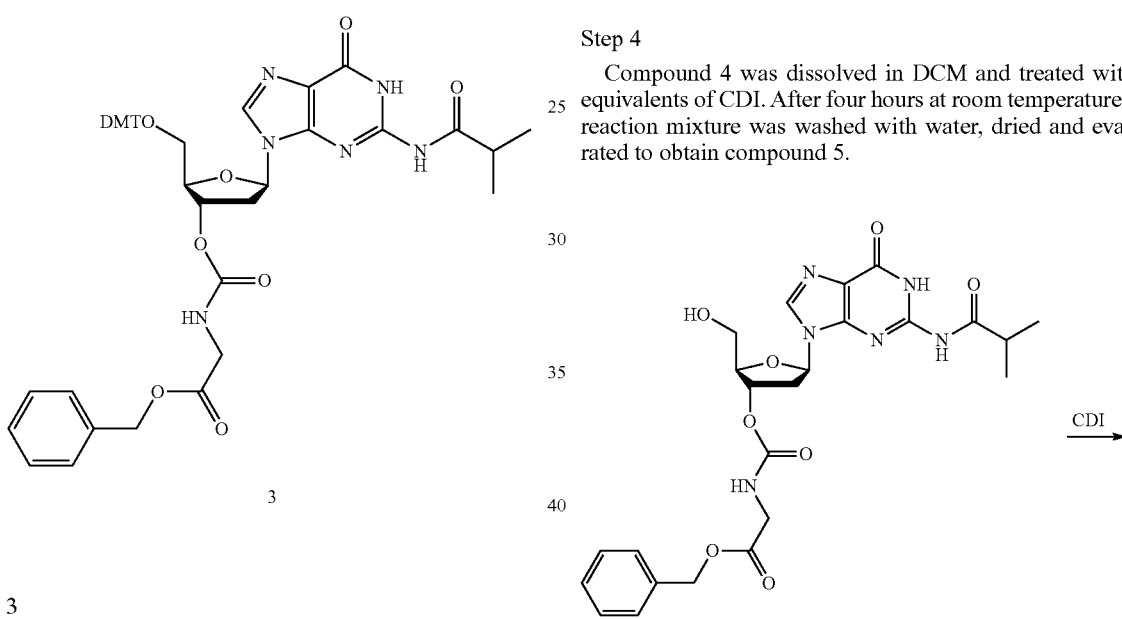
Step 3
Compound 3 was dissolved in 5% dichloroacetic acid (DCA) in DCM and stirred for 15 minutes. The solvents were evaporated and the crude purified by flash chromatography.
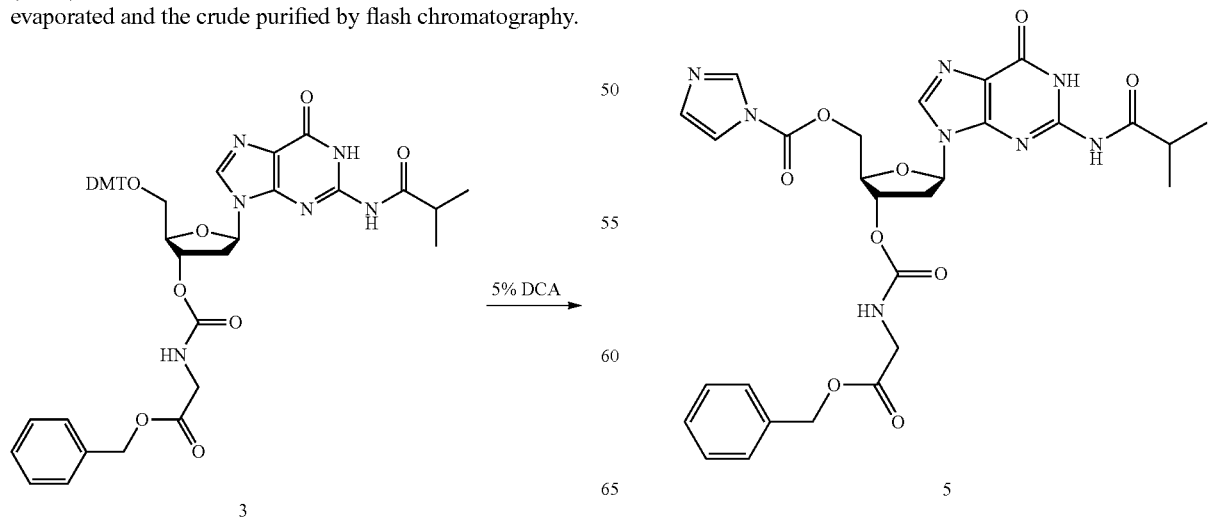

Step 5

Compound 5 was dissolved in DCM and treated with glycine benzyl ester and diisopropyl ethyl amine (DIEA). The reaction was stirred for 20 hours, washed with water and a solution of citric acid. The organic phase was dried and evaporated. The crude was purified by liquid chromatography.

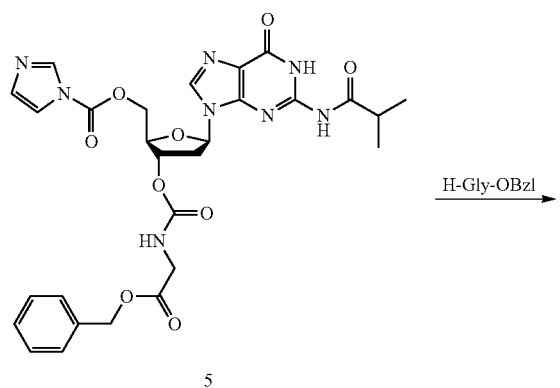

5

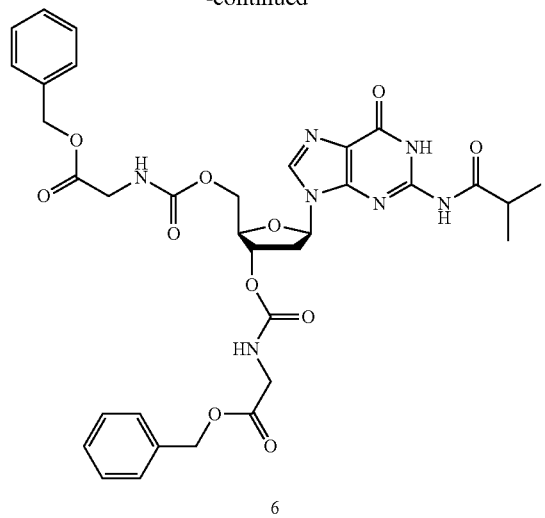

6

Step 6

Compound 6 was dissolved in methanol. Pd on activated charcoal was added and the mixture was stirred for three hours at room temperature under hydrogen. The reaction mixture was filtered and the solvents evaporated to obtain compound 7 (also referred to herein as Compound A1).

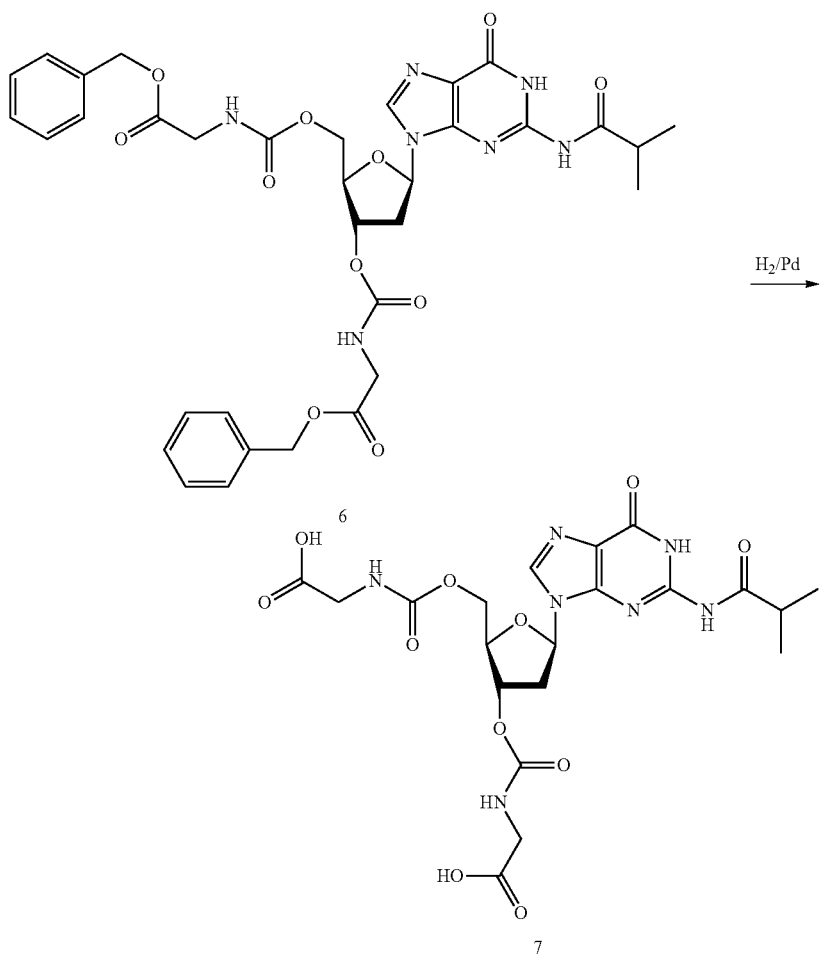

Route B
Step 1

2'-deoxyguanosine hydrate (1') was co-evaporated with pyridine and suspended in dry pyridine. Trimethyl silyl chloride was added and stirred for 30 minutes. Isobutyric anhydride was added and stirred for three hours. Water was added. The mixture was evaporated and dissolved in ethyl ether. After washing with water compound 2' precipitates.

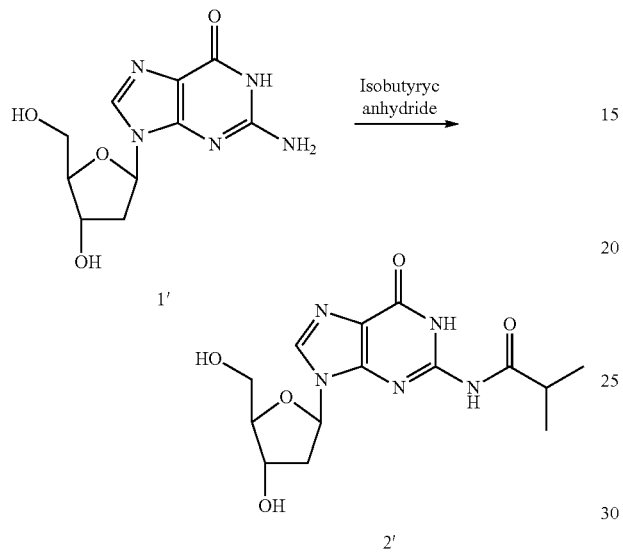

Step 2

Compound 2' was suspended in dry acetonitrile and 8 eq. of CDI were added. The reaction was stirred overnight. Compound 3' precipitates.

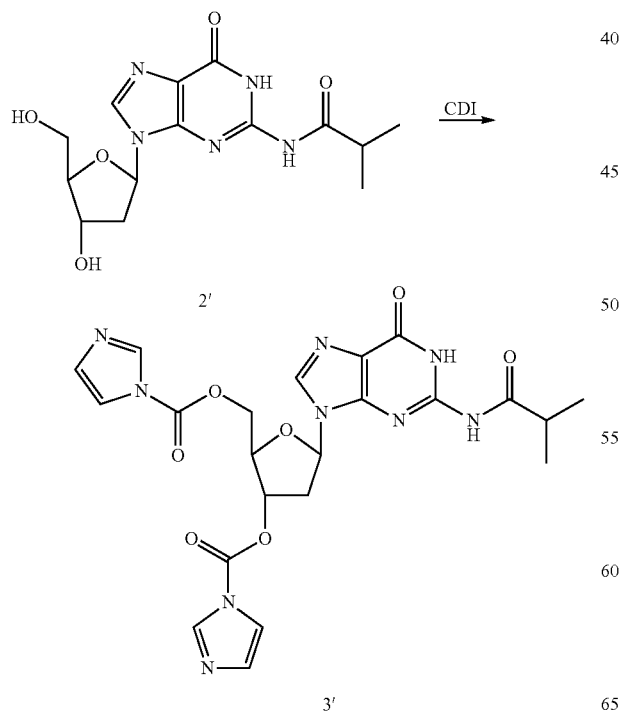

Step 3

Compound 3' was filtered off and re-suspended in dry DCM and treated with glycine benzyl ester and diisopropyl ethyl amine (DIEA). The reaction was stirred for 20 hours, washed with water and a solution of citric acid. The organic phase was dried and evaporated. The crude was purified by liquid chromatography.

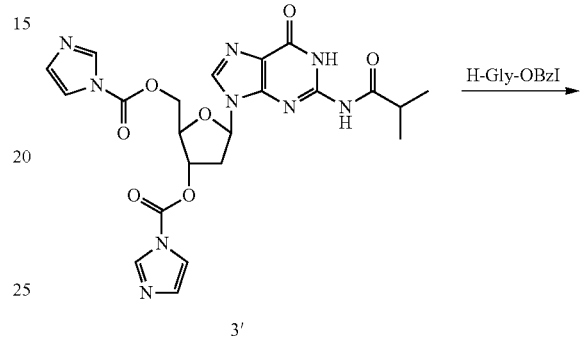

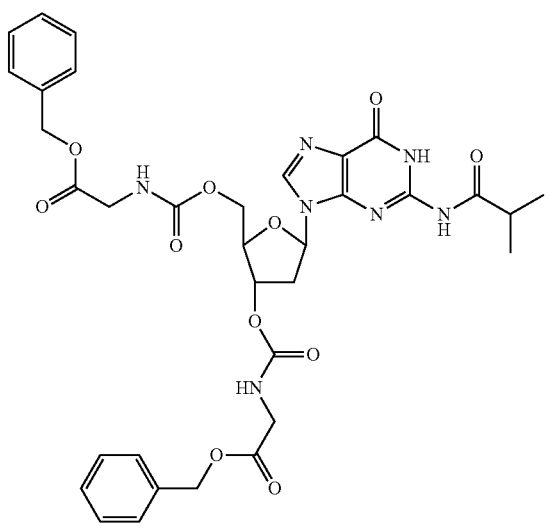

Step 4

Compound 4' was dissolved in methanol. Pd on activated charcoal was added and the mixture was stirred for three hours at room temperature under hydrogen. The reaction mixture was filtered and the solvents evaporated to obtain compound 5' (also referred to herein as Compound A1).

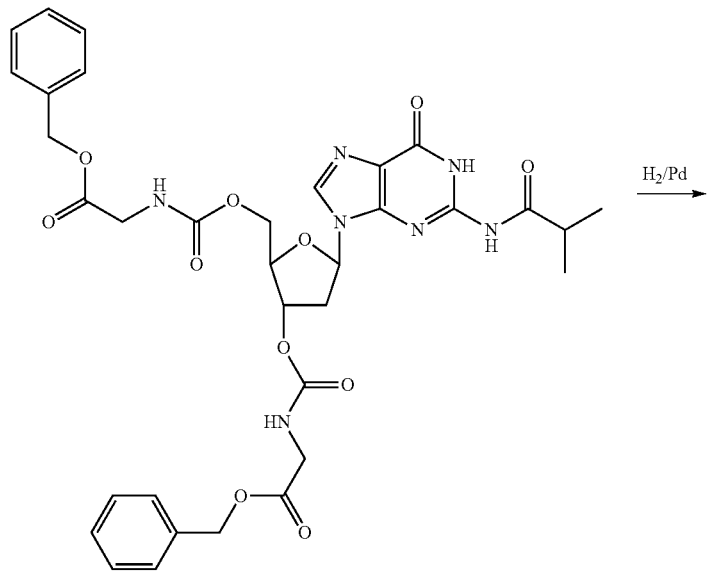
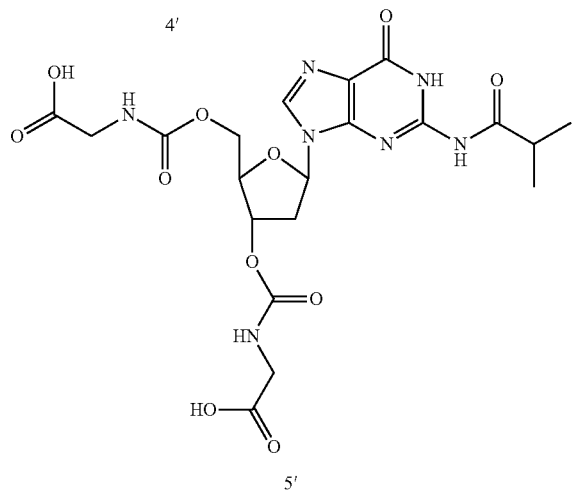
Compound A2
This compound is synthesized using the Route B for the preparation of A1. In Step 3 H-Gly-Gly-OBzl is used instead of H-Gly-OBzl to obtain compound 4:
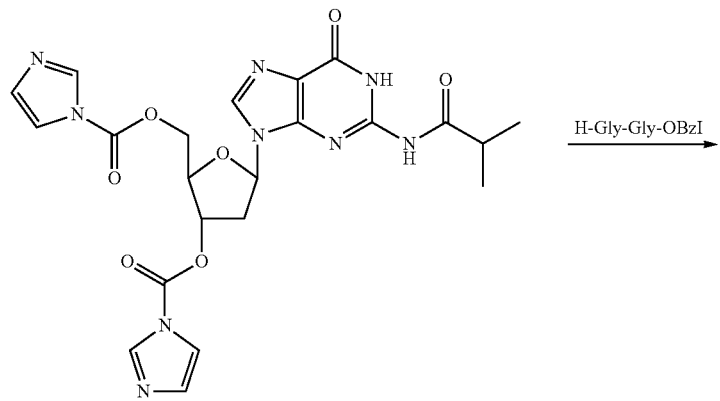

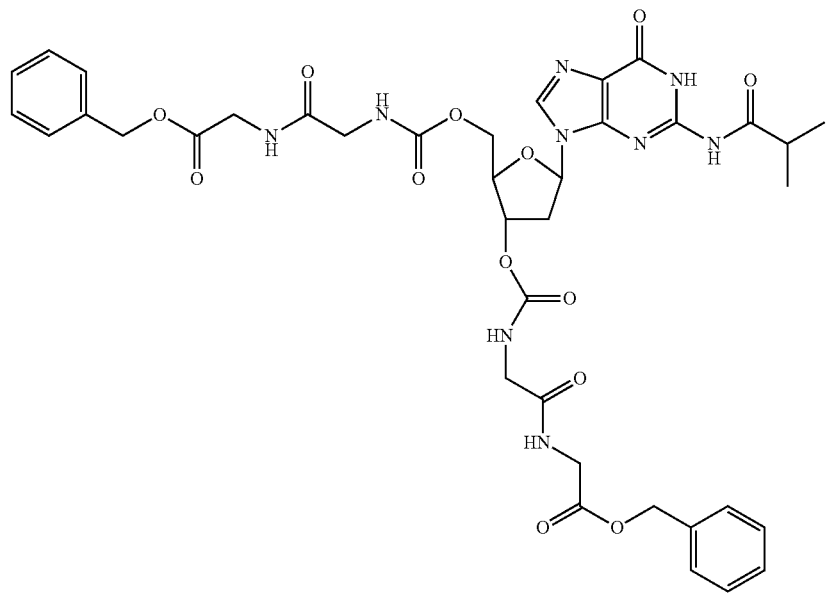
4
Step 4
Compound 4 was dissolved in methanol. Pd on activated charcoal was added and the mixture was stirred for three hours at room temperature under hydrogen. The reaction mixture was filtered and the solvents evaporated to obtain compound 5 (also referred to herein as compound A2).
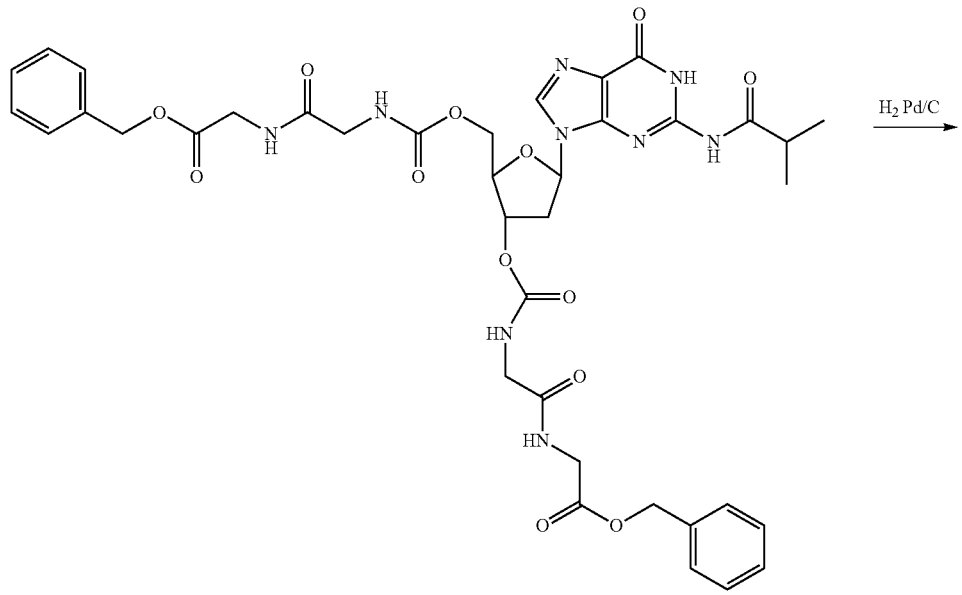
4

-continued

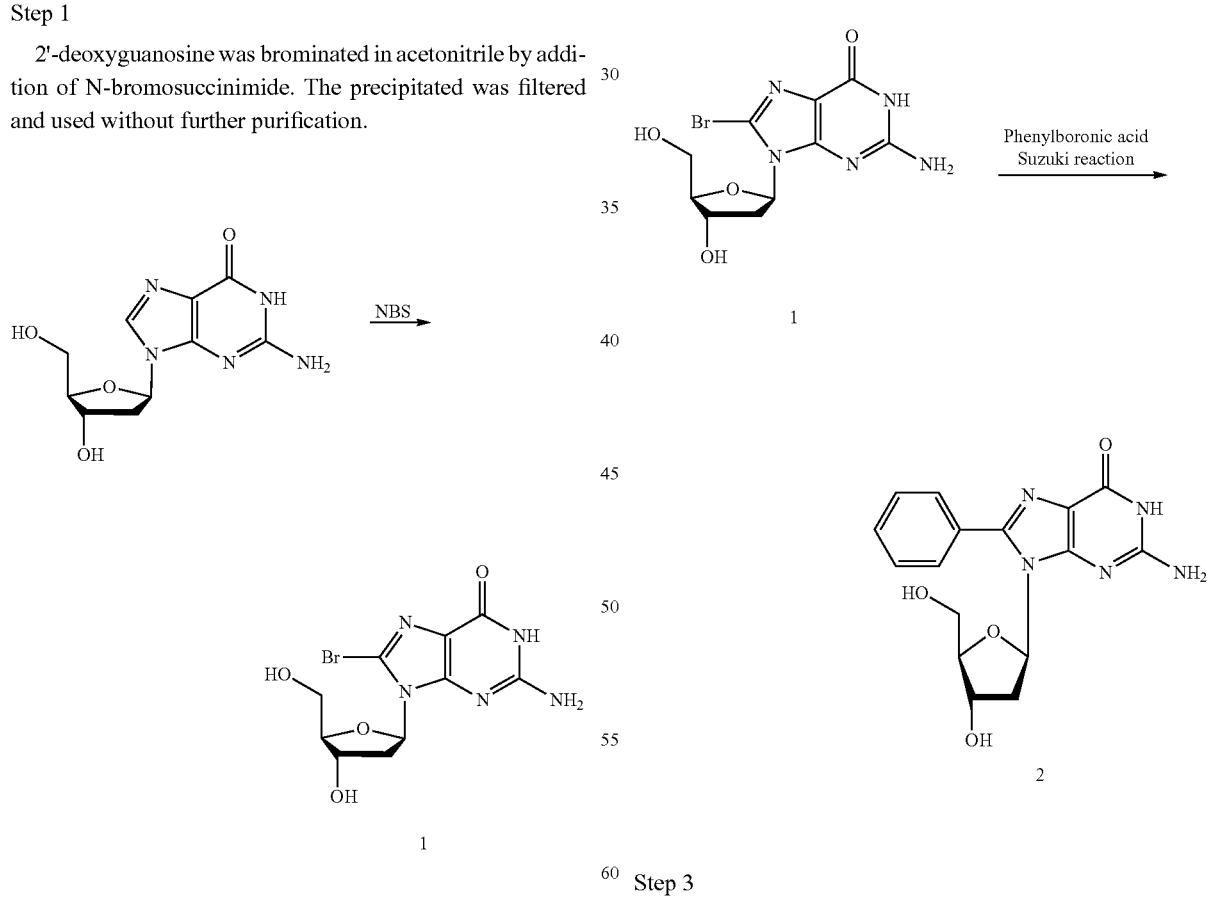

5

Compound A3

Step 1

2'-deoxyguanosine was brominated in acetonitrile by addition of N-bromosuccinimide. The precipitated was filtered and used without further purification.

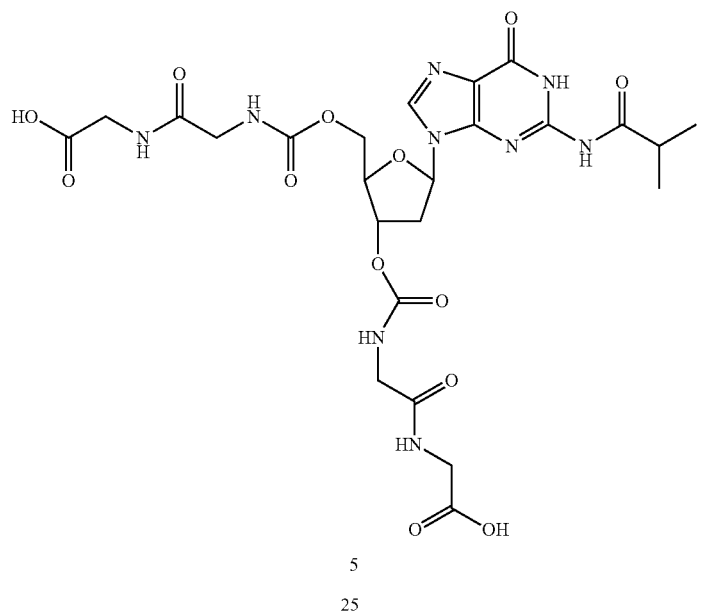

Step 2

Compound 1 was treated with phenyl boronic acid under the well documented Suzuki reaction conditions to obtain compound 2.

Step 3

Compound 2 was treated with trimethyl silyl chloride in pyridine followed by the addition of isobutyric anhydride. At the end of the reaction the trimethyl silyl ether was cleaved and the solvents evaporated. The desired compound was obtained in a high degree of purity by precipitation in water.

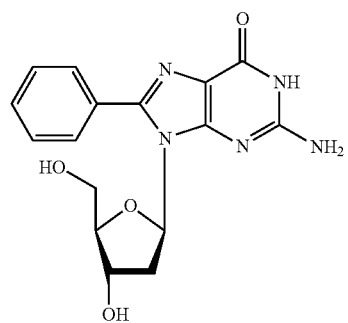 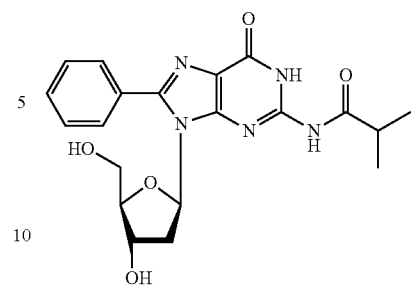
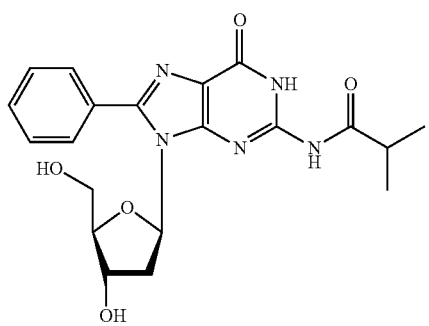 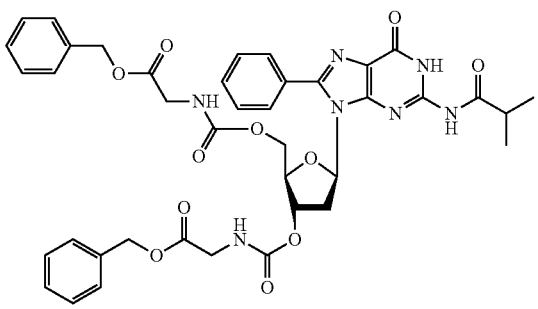
Steps 4 and 5
As described for the preparation of A1 in Route B: steps 2 and 3
Step 6
The procedure used is as step in the preparation of A2. The final product is A3.
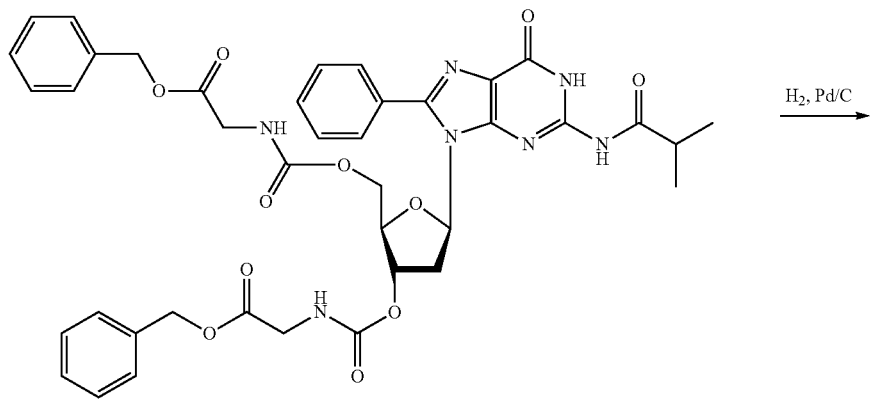
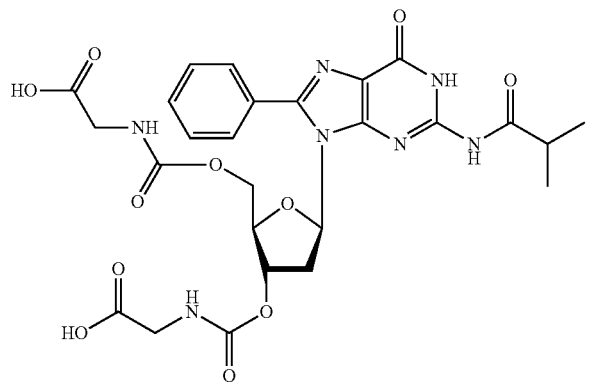

Compounds B1 and B2

2'-deoxyguanosine hydrate was co-evaporated with pyridine and suspended in dry pyridine. Diphenyl phosphite was added and the mixture was stirred for 30 minutes. Methyl glycolate or methyl citrate were added and stirred for 30 minutes. The solvents were evaporated and the crude was dissolved in a solution of 2% iodine in THF/Pyridine and water and stirred for 20 minutes. The solvents were evaporated and ethyl ether and water were added. The aqueous phase was repeatedly washed with ether and lyophilized. The crude was purified in an HPLC system using a RP-C18 preparative column.

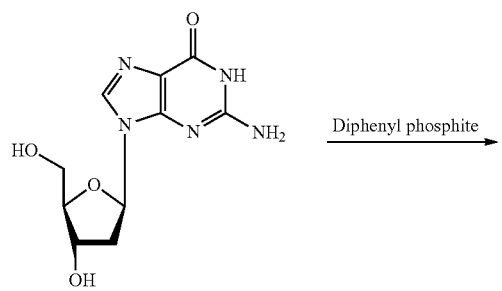

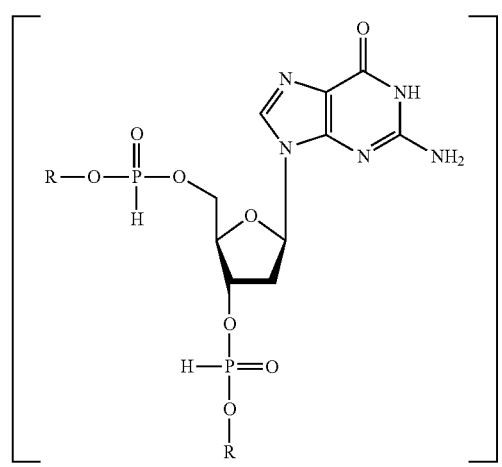

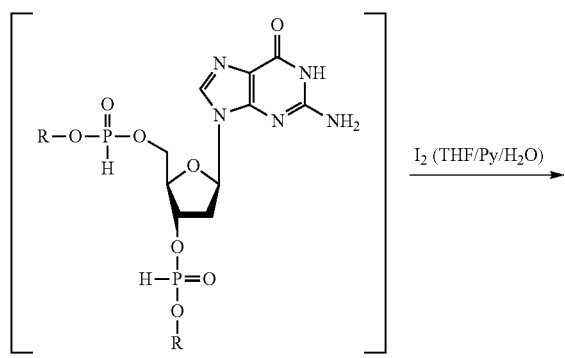

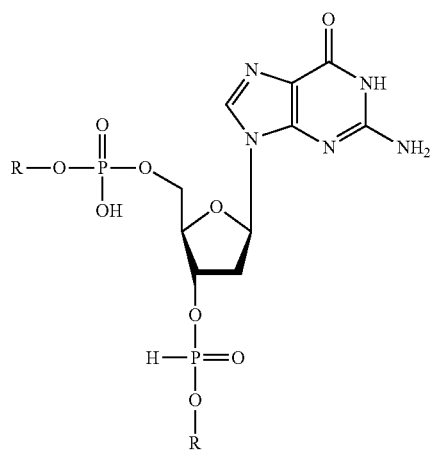

B1: R=

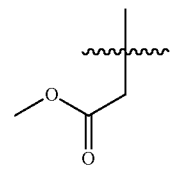 [SMILES: *CC(=O)OC]

B2: R=

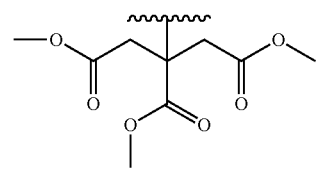

Compound B3

Compound B3 was isolated from the reaction mixture prepared as described before by the same procedure as B1.

Compound C1

Compound 1 was dissolved in dry pyridine. Diphenyl phosphite was added and the mixture was stirred for 30 minutes. Benzyl glycolate was added and stirred for 30 minutes. The solvents were evaporated and the crude was dissolved in a solution of 2% iodine in THF/Pyridine and water and stirred for 20 minutes. The solvents were evaporated and ethyl ether and water were added. The aqueous phase was repeatedly washed with ether and lyophilized. The crude was purified in an HPLC system using a RP-C18 preparative column yielding compound 2 (also referred to herein as Compound C1).

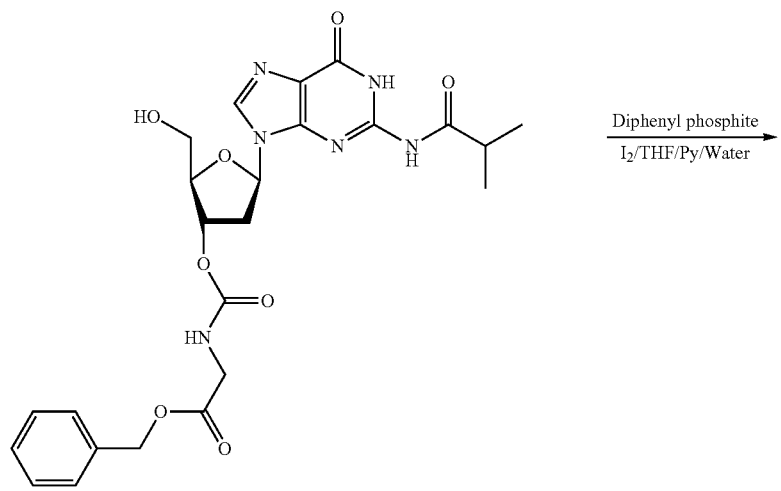

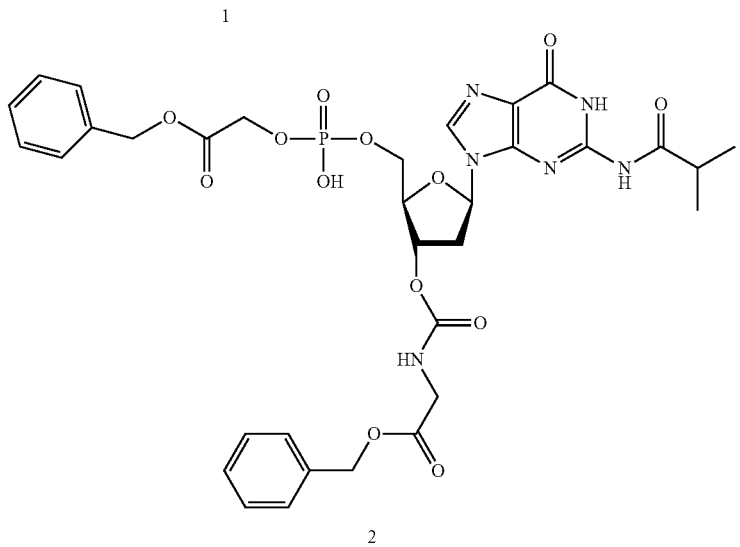

Example 2

Experimental Procedures

Protocols:
Cell-Growth Media:

The growth media used were Luria-Bertani (LB) (1.6% tryptone, 1% yeast extract, 0.5% NaCl). The antibiotics used for selections were used at the following concentrations: 100 μg of ampicillin/mL and 50 μg of kanamycin/mL.

Protein Purification:

Starter cultures of ΔrelA E. coli strain from a laboratory collection (Gropp 2001), over-expressing either pQE30-RelA (pQE30-XA (QIAGEN) carrying E. coli RelA) or pENH385 (pET-21(+) (Novagen) carrying Relseq385 (Mechold 2002)) were grown over-night at 37° C. with shaking. The next day, the cultures were diluted 1:50 in 400 mL LB containing the proper antibiotic and the cells have continued to grow at 37° C. until they reached OD600=~0.6. Then, IPTG (1 mg/mL) was added and the cells were grown at the same conditions for an additional 2-3 hours. After that, the cells were harvested for 10 min at 4000 rpm and the pellet was frozen at −70° C. over-night. The pellet was resuspended in 20 mL of lysis buffer containing 0.5 M NaCl, 20 mM NaH$_2$PO$_4$ (pH 8) and 10 mM imidazole. Also, lysozyme was added to a final concentration of 3 mg/mL together with a tablet of protease inhibitor cocktail (Complete, EDTA-free; Roche) and the cells were then subjected to 3.5 min of sonication in order to break their outer membrane. The resuspended pellet was centrifuged at 10,000 rpm at 4° C. for 10 min to remove the broken membrane. A sample of the soluble fraction was taken and the supernatant was gently mixed with Ni-NTA beads (QIAGEN) at 4° C. for 1 h. The beads were loaded onto a column and washed with 50 mL of washing buffer containing 0.5 M NaCl, 20 mM NaH$_2$PO$_4$ (pH 8) and 20 mM imidazole and a sample was taken. Elution of the bound protein was achieved by the addition of 30 mL of elution buffer, containing 0.5 M NaCl, 20 mM NaH$_2$PO$_4$ (pH 8) and 250 mM imidazole. The elution fractions were run on 12% Acryl/Bis gel and the fractions containing the most protein were loaded onto a cellulose tubular membrane, mwco 12,000-14,000 (Cellu Sep) and stirred inside dialysis buffer, containing 100 mM Tris-Ac (pH 8.5), 10 mM EDTA, 1 mM DTT and 25% glycerol (two over-night runs at 4° C.). After dialysis, the concentration of the purified proteins was determined using Bradford Reagent (OD595).

Ribosome Preparation:

Ribosomes were prepared as described by Block and Haseltine 37 with the following modifications: cells were grown in LB medium with shaking at 37° C. At an OD600 of 1.5, 2 liters of the cell culture was pelleted at 4° C. (6000 rpm for 20 min) and frozen over-night at −70° C. Next, the pellet was resuspended in 60 mL of cold ribosome buffer containing 100 mM Tris-acetate (pH 8.0), 10 mM Mg(OAc)$_2$, and 1 mM dithiothreitol. Also, lysozyme was added to a final concentration of 3 mg/mL together with a tablet of protease inhibitor cocktail (Complete, EDTA-free; Roche), and cells were lysed by vigorous vortexing. Cells were then sonicated on ice for 3.5 min and pelleted at 4° C. (15,000 rpm for 40 min). A sample of the supernatant representing the soluble proteins before fractionation was saved for further analysis, while the rest of the supernatant was centrifuged in a Beckman Ti-65 rotor (30,000 rpm) at 4° C. for 4 h. The pellet was scraped and kept stirred at 4° C. in 10 mL of ribosome buffer overnight. The following day, the supernatant was pelleted at 10,000 rpm at 4° C. for 15 min in order to remove excess membrane residues and the supernatant was saved on ice. A Ribosome buffer containing 40% sucrose was prepared and 5 mL were loaded into 30 mL polycarbonate Ultra bottles (Sorvall Instruments). Thereafter, the supernatant was loaded on top of the sucrose buffer and the bottles were centrifuged, using a Beckman Ti-65 rotor (32,000 rpm) at 4° C. for 4 h. The pellet was then suspended in 2 mL of ribosome buffer and the ribosomes were frozen and stored at −70° C. Protein concentrations in the ribosomal fraction were determined based on RNA measurements in an ND-1000 Spectrophotometer (Nano-Drop).

In Vitro (p) ppGpp Accumulation Assay:

5× reaction mixture containing 2.5 mM GTP, 20 mM ATP, 200 mM Tris-HCl (pH 7.4), 5 mM DTT, 50 mM MgCl$_2$, 50 mM KCl, 135 mM (NH$_4$)$_2$SO$_4$ and α-32P GTP (0.1 μl per reaction) was freshly prepared. 0.5-1 μg of either RelA or Relseq385 together with 1× reaction mixture and 30 μg of ribosomes (if necessary) were mixed in a total volume of 20 μl. Each reaction also contained a (p) ppGpp analogue in a concentration ranging between 0-10 mM. The reactions were incubated at room temperature for a period of either 5 min (Relseq385) or 60 min (RelA). The reactions were stopped by the addition of 5 μl Formic acid. 5 μl of each reaction was loaded onto Cellulose PEI (Merck) and run for 2 hours in 1.5 M KH$_2$PO$_4$. The data was analyzed using image reader 1000 V1.8 and the (p) ppGpp content was determined using the TINA 2.0 software (Raytest, Strauben-Hardt, Germany).

Induction of Sporulation by the Stringent Response to Partial Deprivation of Amino Acids Cells were grown to an OD600 of 0.5. They were then washed with synthetic medium on a membrane filter and suspended in synthetic medium lacking amino acids in order to induce them to sporulate in the presence and the absence of inhibitors. Sporulation was monitored by fluorescence microscopy.

Example 3

Figure 1B:
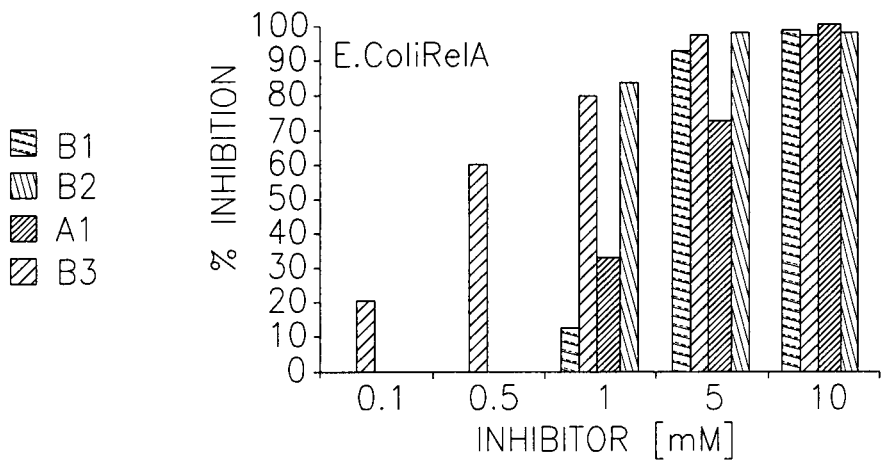
Figure 1C:

Effects of Compounds of the Invention on Rel Proteins from Gram Positive and Gram Negative Bacteria The newly synthesized compounds were tested on Rel proteins from both gram positive and gram negative bacteria. In every case the inhibitory efficiency was higher than that previously reported. FIG. 1 shows the percentage of inhibition of selected compounds in three different systems. RelA from *E. Coli*, Rel/Spo from *D. Radiodurance* and the N-terminal domain of Rel/Spo from E. Equisimilis (Rel$_{Seq1-385}$).

Figure 2A:
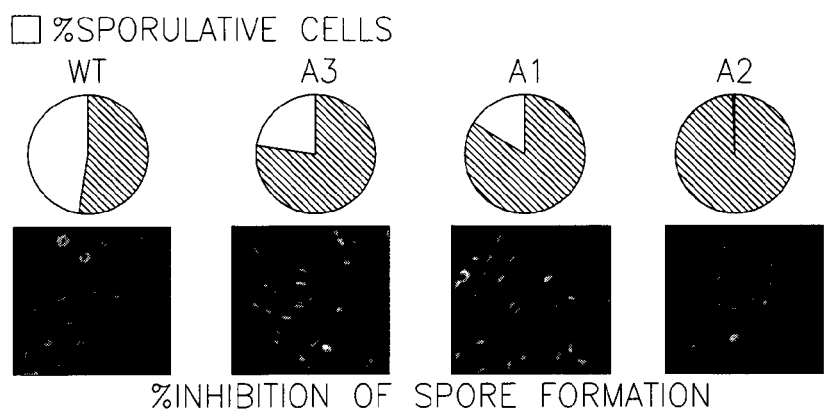
FIG. 2A: effect of compounds A1, A2 and A3 on the start of the sporulating process (two hours after inducing sporulation).

In order to evaluate the effects of compounds of the invention on sporulation, wild type bacteria were induced to sporulate in the presence of compounds A1, A2 and A3 and the process was monitored using fluorescence microscopy. FIG. 2A shows the effect of compounds A1, A2 and A3 on the start of the sporulating process (two hours after inducing sporulation).

Figure 2B:
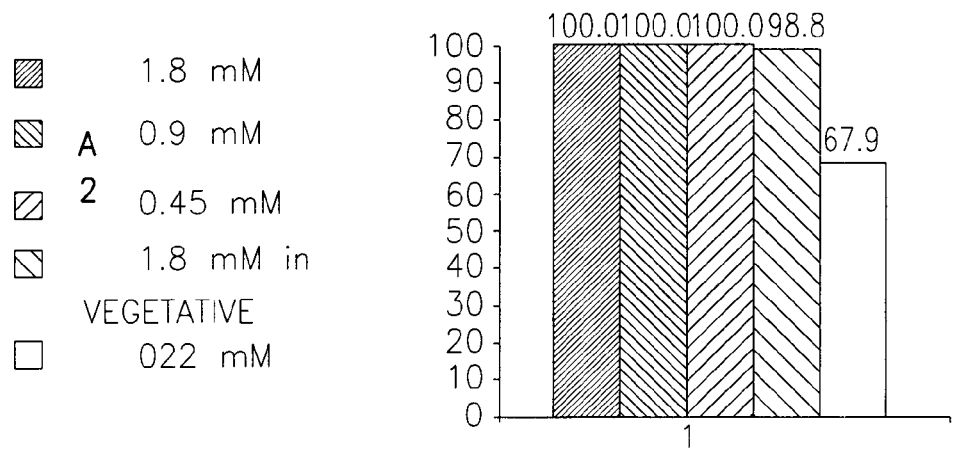
FIG. 2B-C: effect of different concentrations of A2 on spore formation 24 hours after inducing sporulation
Figure 2C:
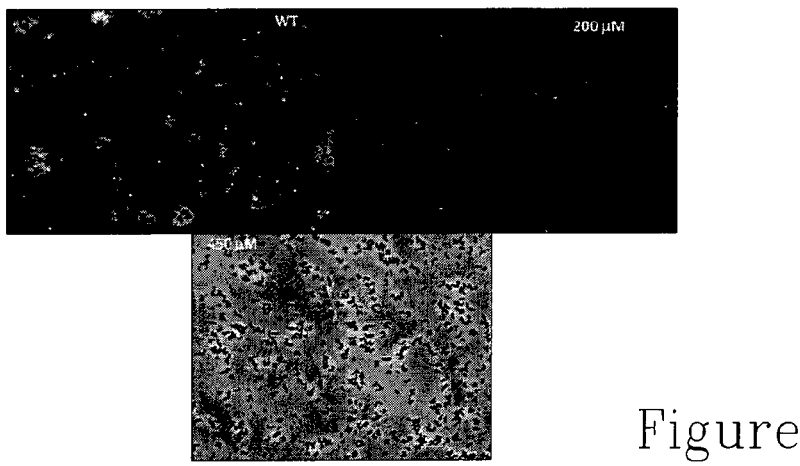

In order to further evaluate the effect of compounds A2 on sporulation, wild type bacteria were induced to sporulate in the presence of different concentrations (from 200 to 1.8 mM) of compound A2 and the process was monitored using fluorescence microscopy. With the aim of learning about the fate of the spores formed in the previously described cultures, an aliquot from the cell culture was taken and subjected to heat treatment (heat shock). The treatment included exposure of the cultures to 80° C. for 15 minutes and further plating on LB plates. After incubating the plates for 15 hours at 37° C., the colony forming units (CFUs) were quantified and the percent of mature spore formation was calculated (FIG. 2B-C). As seen, even the lowest tested concentration of A2 (0.22 mM) significantly reduced by about 70% the formation of mature spores, with the rest of the tested concentrations inhibiting 100% of sporulation.

Figure 3:
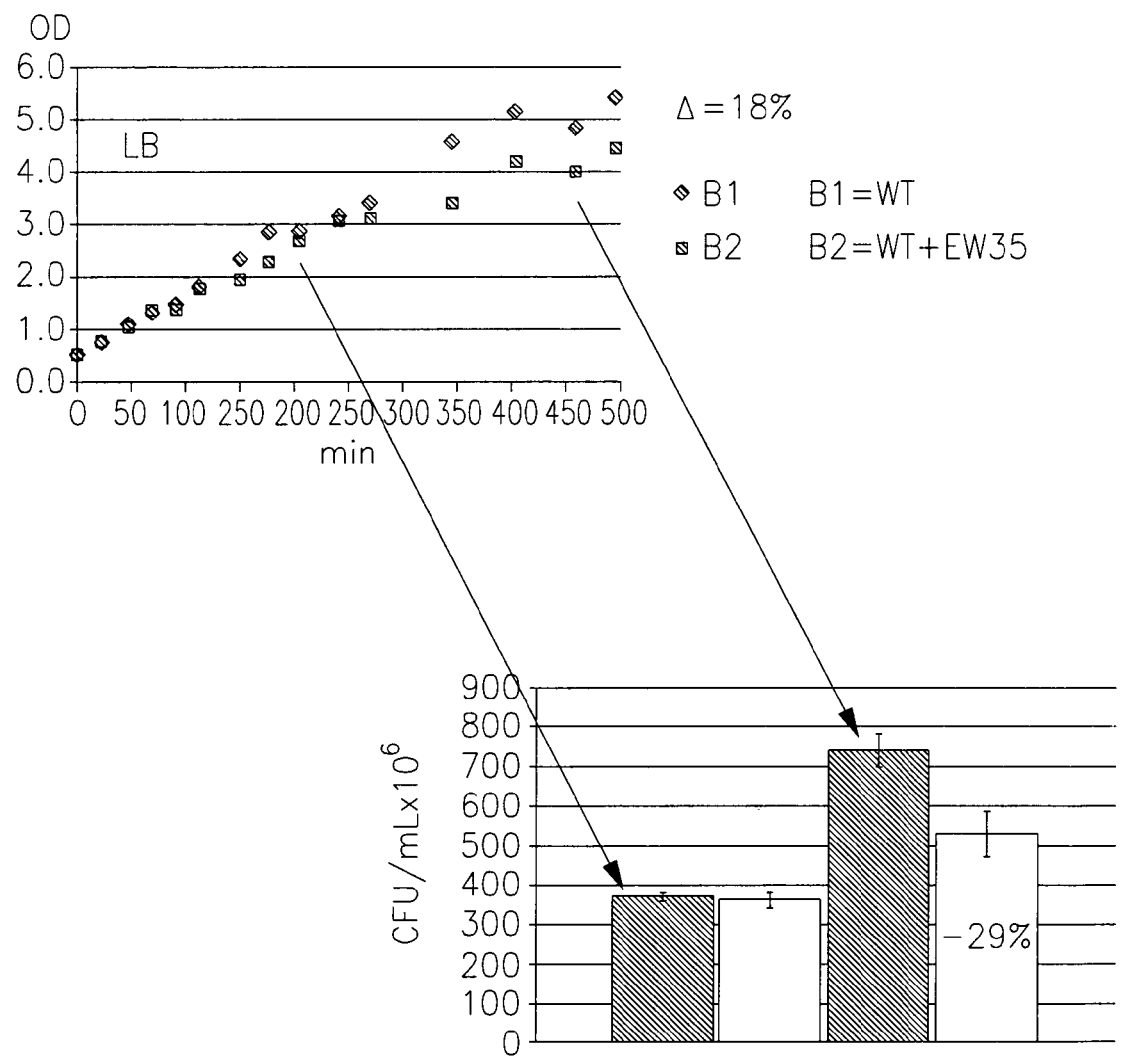
FIG. 3: shows the effect of compound A2 on growth and survival of *B. subtilis* growing in LB medium.

The effect of A2 on growth and survival of *B. subtilis* growing in LB medium was then evaluated. Bacteria were grown overnight at 23° C. and diluted to an OD$_{600}$ of 0.05. Subsequently, bacteria were further grown at 37° C. and A2 (1.8 mM) was added at an OD$_{600}$ of 0.2. Bacterial growth was then continuously monitored by measuring the turbidity of the medium at 600 nm (OD$_{600}$). Samples were taken and plated on LB plates. The plates were incubated at 37° C. for 15 hours. Colony forming units (CFU) were counted and compared to the untreated culture. As shown in FIG. 3, compound A2 substantially reduced the number of CFUs.

Example 4

Inhibition of ppGpp Synthesis by Compound A2 In Vitro

Figure 4:
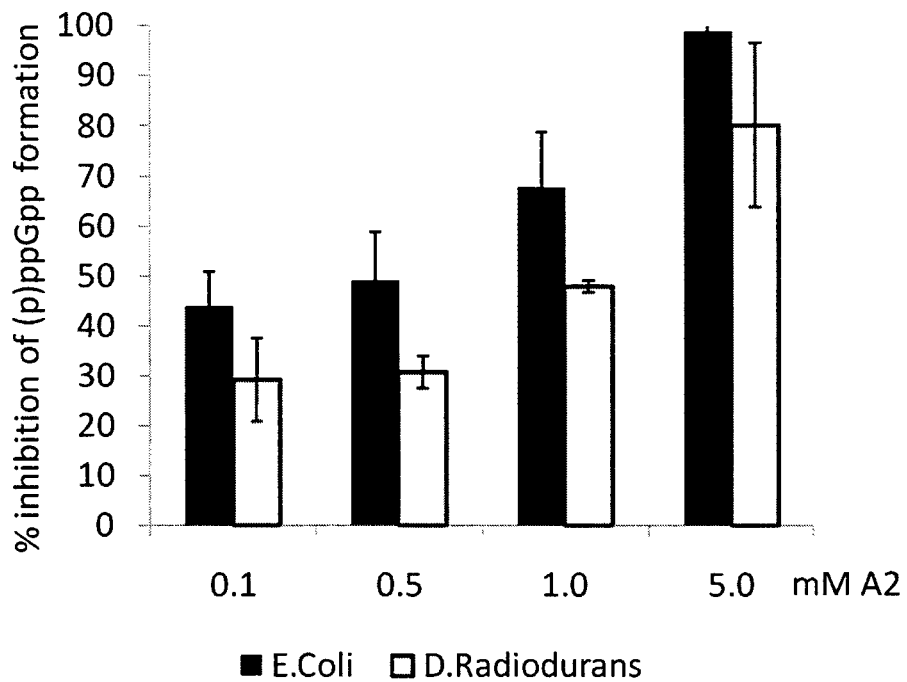
FIG. 4: shows the % inhibition of ppGpp synthesis in gram negative bacteria *E. Coli* and gram positive bacteria *D. radiodurans* in the presence of increasing concentrations of compound A2.

Inhibition of the synthetase activity of Rel proteins from gram negative bacteria *E. coli* and gram positive bacteria *D. radiodurans* was assessed as described previously. The results are shown in FIG. 4.

Example 5

Inhibition of ppGpp Synthesis by Compound A2 in *B. Subtilis*

Figure 5:
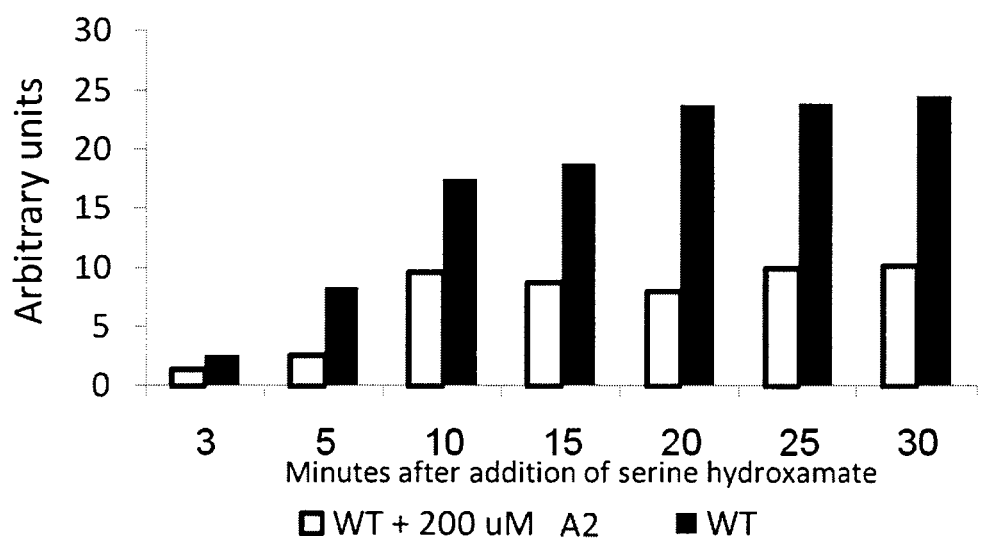
FIG. 5: shows the inhibition of ppGpp synthesis in *B. subtilis* by 0.2 mM compound A2.

*B. subtilis* bacteria were grown in the presence and in the absence of 200 μM compound A2. After incubation with radioactive phosphate, serine hydroxamate was supplemented to the growth medium in order to induce the stringent response. Aliquots were taken at different time points, loaded on PEI TLC plates and developed. Radioactivity was quantified and the effect of compound A2 evaluated. The results are shown in FIG. 5.

Example 6

Effect of A2 on Bacterial Survival

Figure 6:
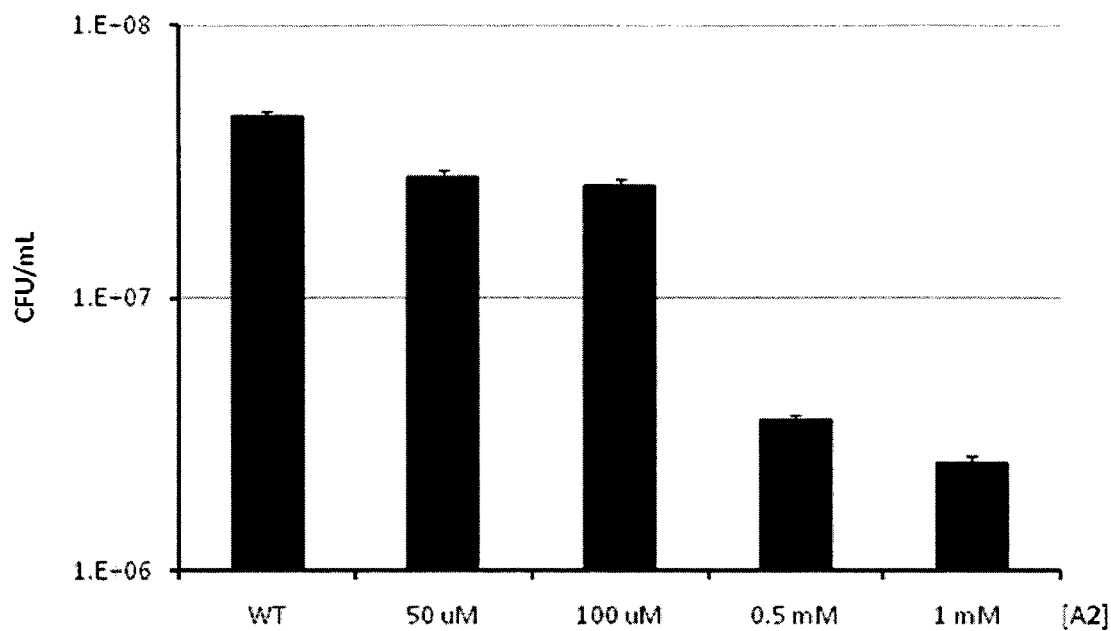
FIG. 6: shows the effect of increasing concentrations of compound A2 on bacterial survival.

Bacteria were grown in CH medium and samples were taken and plated on LB plates after 24 hours of growth. The plates were incubated at 37° C. for 15 hours. Colony forming units (CFU) were counted and compared to the untreated culture. FIG. 6 shows the results of the CFU counting. After 24 hours of growth, the CFU/mL of the treated cultures decreases in a dose dependent fashion.

Example 7

A2 Stops Sporulation Regardless of the Time-Point of Addition to the Culture

Figure 7:
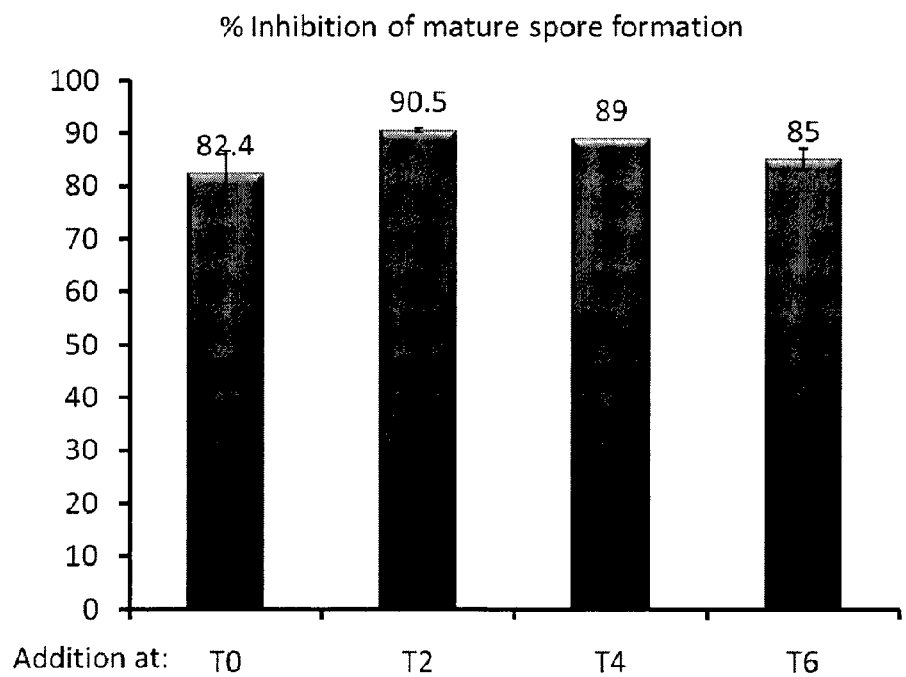
FIG. 7: shows the inhibitory effect of compound A2 on mature spore formation.

The influence of the timing of addition of A2 was evaluated. Bacteria were induced to sporulate and A2 (1.8 mM) was added to the cultures every two hours (at T=0, T=2, T=4 and T=6). After growing overnight the cultures were heated and plated on LB plates. Surprisingly, quantification of CFU after 15 hours of incubation indicated that in every case the addition of A2 inhibited the formation of mature spores by more than 80% (FIG. 7). This unexpected finding suggests that, if RelA's activity is being inhibited, ppGpp is essential for the completion of the sporulation process.

Example 8

Cytotoxicity of Compound A2

Cytotoxicity of compound A2 on eukaryotic (A431) and prokaryotic cells (*B. Subtilis*) was determined by using the methylthiazolyldiphenyl-tetrazolium bromide (MTT) assay. Bacteria were grown in CH medium and samples were taken and plated on LB plates after 24 hours of growth. The plates were incubated at 37° C. for 15 hours. Colony forming units (CFU) were counted and compared to the untreated culture. Viable bacterial cells are counted as CFU/mL: colony forming units per milliliter. Each CFU is equivalent to viable cell.

Figure 8:
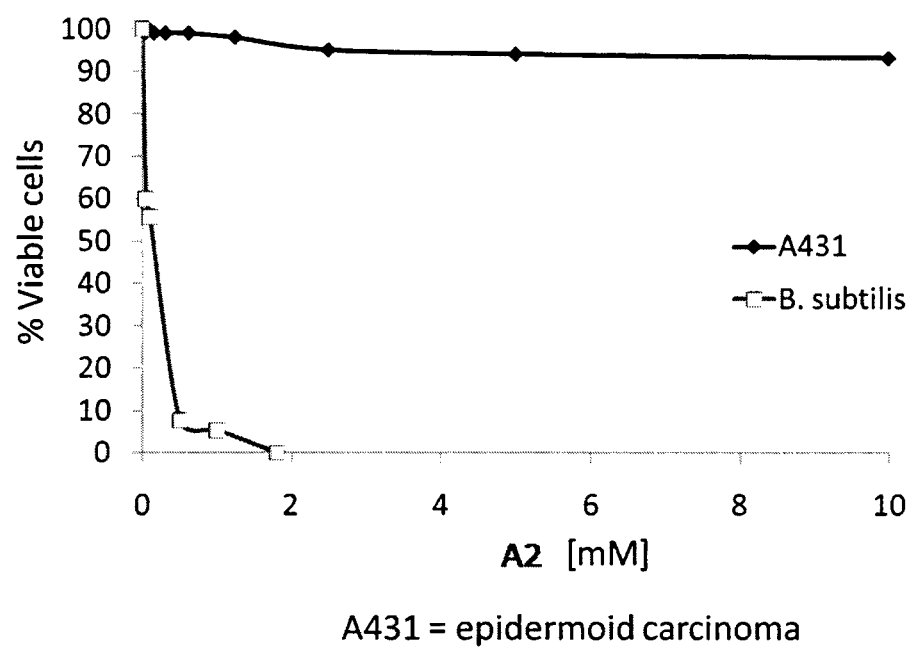
FIG. 8: shows the cytotoxic effect of compound A2 in A431 Epidermoid carcinoma cells (eukaryotic) and in *B. Subtilis* (prokaryotic).

In a standard procedure, the cell line (A431: epidermoid carcinoma) was incubated for 24 hours in 37° C. and 5% $CO_2$. Subsequently, compound A2 was added to the wells in up to 10 different concentrations. Subsequent to incubation of cells with A2 for an additional 72 hours, the MTT reagent was added. Extraction of MTT with isopropanol and further measurement of the absorption resulted in an estimate of the amount of live cells in each well. The results are shown in FIG. 8. As seen, Compound A2 was completely cytotoxic to *B. Subtilis* cells but not to A431 cells.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES

1) Cashel, M., and Gallant, J. (1969). Two compounds implicated in the function of the RC gene of *Escherichia coli*. Nature 221, 838-841.
2) Cashel, M., Lazzarini, R. A., and Kalbacher, B. (1969). An improved method for thin-layer chromatography of nucleotide mixtures containing $^{32}$P-labelled orthophosphate. *J. Chromatogr.* 40, 103-9.
3) Cashel et al., (1970). The control of ribonucleic acid synthesis in *Escherichia coli*. V. Characterization of a nucleotide associated with the stringent response, *J. Biol. Chem.* 2309-2318.
4) Cashel, M. G. D., Hernandez, V J, Vinella, D. (1996). The Stringent response. *E. coli* and *Salmonella typhymurium*: cellular and molecular biology, 2nd ed., pp. 1458-1496.
5) Gentry, D. R., Hernandez, V. J., Nguyen, L. H., Jensen, D. B., and Cashel, M. (1993). Synthesis of the stationary-phase sigma factor $\sigma^s$ is positively regulated by ppGpp. *J. Bacteriol.* 175, 7982-7989.
6) Metzger, S., Dror, I. B., Aizenman, E., Schreiber, G., Toone, M., Friesen, J. D., Cashel, M., and Glaser, G. (1988). The nucleotide sequence and characterization of the relA gene of *Escherichia coli. J. Biol. Chem.* 263, 15699-15704.
7) Pedersen, F. S., and Kjeldgaard, N. O. (1977). Analysis of the relA gene product of *Escherichia coli. Eur. J. Biochem.* 76, 91-97.
8) Haseltine, W. A., and Block, R. (1973). Synthesis of guanosine tetra and penta phosphate requires the presence of a codon specific, uncharged transfer ribonucleic acid in the acceptor site of ribosomes. *Proc. Natl. Acad. Sci. USA* 70, 1564-1568.
9) Gentry, D. R., and Cashel, M. (1995). Cellular localization of the *Escherichia coli* SpoT protein. *J. Bacteriol.* 177, 3890-3893.
10) Metzger, S., Sarubbi, E., Glaser, G., and Cashel, M. (1989). Protein sequences encoded by the relA and the spoT genes of *Escherichia coli* are interrelated. *J. Biol. Chem.* 264, 9122-9125.
11) Seyfzadeh, M., Keener, J., and Nomura, M. (1993). spoT-dependent accumulation of guanosine tetraphosphate in response to fatty acid starvation in *Escherichia coli. Proc. Natl. Acad. Sci. USA* 90, 11004-11008.
12) Xiao, H., Kalman, M., Ikehara, K., Zemel, S., Glaser, G., and Cashel, M. (1991). Residual guanosine 3',5'-bispyrophosphate synthetic activity of relA null mutants can be eliminated by spoT null mutations. *J. Biol. Chem.* 266, 5980-5990.
13) Mechold, U., Cashel, M., Steiner, K., Gentry, D., and Malke, H. (1996). Functional analysis of a relA/spoT gene homolog from *Streptococcus equisimilis. J. Bacteriol.* 178, 1401-1411.
14) Mechold, U., and Malke, H. (1997). Characterization of the stringent and relaxed responses of *Streptococcus equisimilis. J. Bacteriol.* 179, 2658-2667.
15) Mittenhuber, G. (2001). Comparative genomics and evolution of genes encoding bacterial (p) ppGpp synthetases/hydrolases (the Rel, RelA and SpoT proteins). *J. Mol. Microbiol. Biotechnol.* 3, 585-600.
16) Wendrich, T. M., and Marahiel, M. A. (1997). Cloning and characterization of a relA/spoT homologue from *Bacillus subtilis. Mol. Microbiol.* 26, 65-79.
17) Gentry, D., Li, T., Rosenberg, M., and McDevitt, D. (2000). The rel gene is essential for in vitro growth of *Staphylococcus aureus. J. Bacteriol.* 182, 4995-4997.
18) Harris, B. Z., Kaiser, D., and Singer, M. (1998). The guanosine nucleotide (p) ppGpp initiates development and A-factor production in *Myxococcus xanthus. Genes Dev.* 12, 1022-1035.
19) van der Biezen, E. A., Sun, J., Coleman, M. J., Bibb, M. J., and Jones, J. D. (2000). *Arabidopsis* RelA/SpoT homologs implicate (p) ppGpp in plant signaling. *Proc. Natl. Acad. Sci. USA* 97, 3747-3752.
20) Givens, R. M., Lin, M. H., Taylor, D. J., Mechold, U., Berry, J. O. and Hernandez, V. J. (2004). Inducible expression, enzymatic activity, and origin of higher plant homologues of bacterial RelA/SpoT stress proteins in *Nicotiana tabacum. J. Biol. Chem.* 279, 7495-7504.
21) Takahashi, K., Kasai, K. and Ochi, K. (2004). Identification of the bacterial alarmone guanosine 5'-diphosphate 3'-diphosphate (ppGpp) in plants. *Proc. Natl. Acad. Sci. USA* 101, 4320-4324.

22) J. Errington. Regulation of endospore formation in *Bacillus subtilis*. *Nat Rev Microbiol* 1(2), 117-26 (2003).
23) Freese et al. Partial purine deprivation causes sporulation of *Bacillus subtilis* in the presence of excess ammonia, glucose, and phophate. *J Gen Microbiol.* 115:193-205 (1979a).
24) Wexselblatt et al., *Bioorg. Med. Chem.* (2010) 18, 4485-4497
25) Glaser et al., PCT/IL2009/000309 WO 2009/116044 "Compounds for Treating Bacterial Infections".
26) Rodionov et al., *J. Bacteriology* (1995) 4224-4229.

What is claimed is:

1. A compound represented by the structure of formula (I):

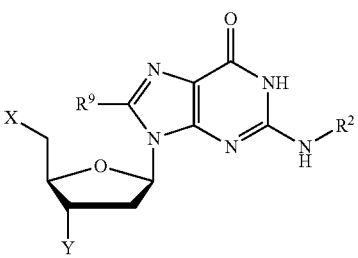
(I)

wherein:
(a) X is

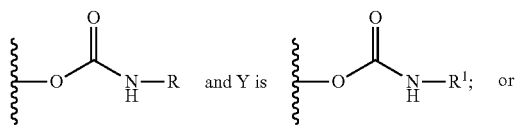

(b) X is

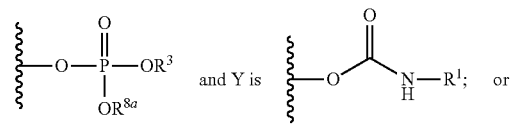

(c) X is

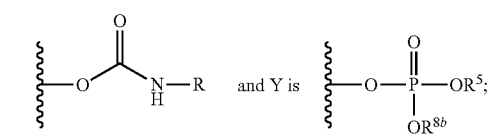

R and $R^1$ are each independently selected from the group consisting of:

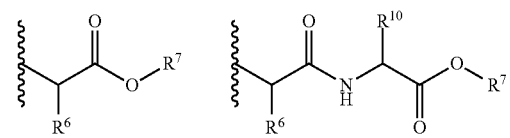

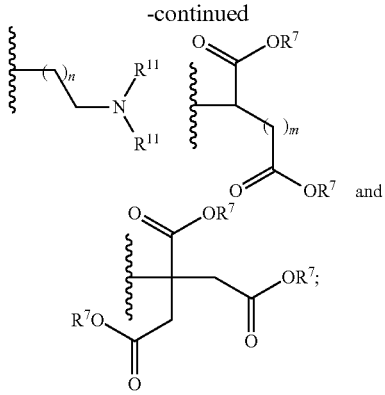

$R^2$ is H or

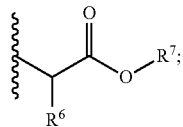

$R^3$ and $R^5$ are each independently H or a moiety selected from the group consisting of:

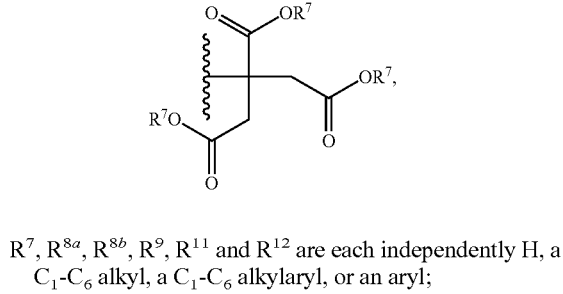

$R^7$, $R^{8a}$, $R^{8b}$, $R^9$, $R^{11}$ and $R^{12}$ are each independently H, a $C_1$-$C_6$ alkyl, a $C_1$-$C_6$ alkylaryl, or an aryl;
$R^6$ and $R^{10}$ are each independently a side chain of a natural or unnatural amino acid;
n is 1, 2, 3, 4, 5 or 6; and
m is 1 or 2;
including salts, hydrates, solvates, polymorphs, optical isomers, geometrical isomers, enantiomers, diastereomers, complexes and mixtures thereof.

2. The compound according to claim 1, wherein R and $R^1$ are each independently
(a) a monocarboxylic acid derivative of formula (b) a dicarboxylic acid derivative of formula

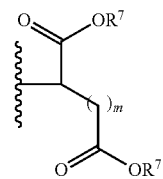

wherein m is 1;

(c) a tricarboxylic acid derivative of the formula

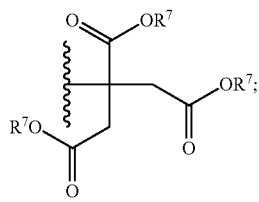

(d) a dipeptide derivative of formula

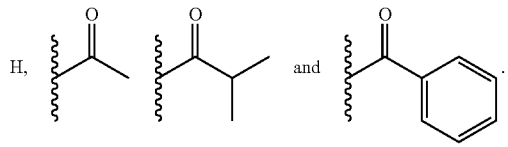

wherein $R^6$ and $R^{10}$ are the same or different and are each independently a side chain of glutamic acid, valine, lysine or glycine; or (e) dimethylamino propyl.

3. The compound according to claim 1, wherein $R^2$ is selected from:

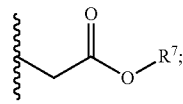

4. The compound according to claim 1, wherein $R^2$ is H or —CO—CH(CH$_3$)$_2$.

5. The compound according to claim 1, wherein $R^3$ and $R^5$ are each independently selected from the group consisting of:

(a) H;

(b) a monocarboxylic acid derivative of formula

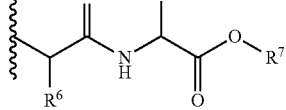

(c) a dicarboxylic acid derivative of formula

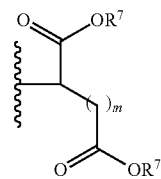

wherein m is 1;

(d) a tricarboxylic acid derivative of formula

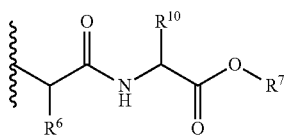

wherein $R^7$ is H, methyl, ethyl or benzyl.

6. The compound according to claim 1, wherein $R^{8a}$ and $R^{8b}$ are each independently H or methyl.

7. The compound according to claim 1, wherein $R^7$ is independently at each occurrence H, methyl, ethyl or benzyl.

8. The compound according to claim 1, wherein $R^9$ is H or phenyl.

9. The compound according to claim 1, which is represented by the structure of formula A:

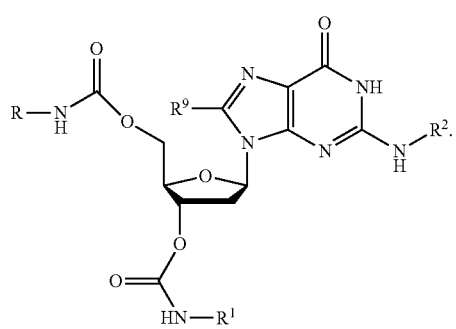

10. The compound according to claim 9, wherein R and $R^1$ are each independently

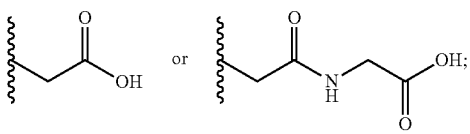 [SMILES: *CC(=O)O ; "or" ; *CC(=O)NCC(=O)O]

or wherein R and $R^1$ are each a monocarboxylic acid derivative of formula

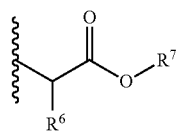

or a dipeptide derivative of the formula

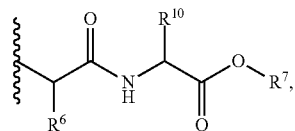

and R² is —CO—CH(CH₃)₂.

11. The compound according to claim 9, which is represented by the structure of formula A1, A2 or A3:

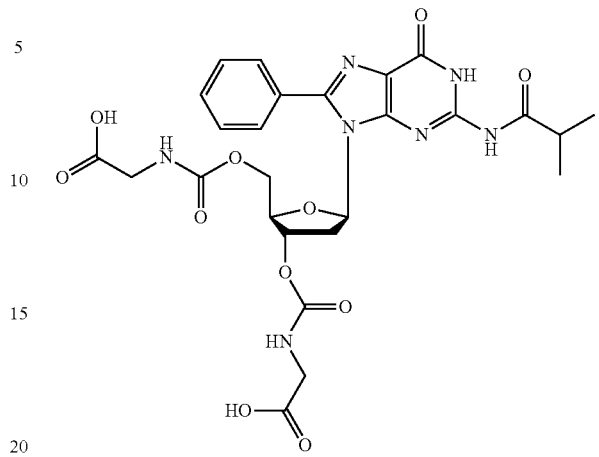

12. The compound according to claim 1, which is represented by the structure of formula C:

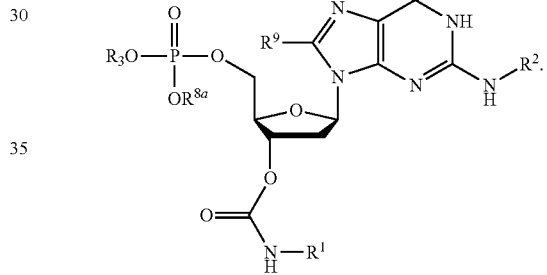

13. The compound according to claim 12, wherein R³ is a monocarboxylic acid derivative of formula

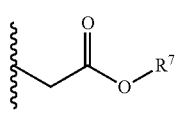

wherein R⁷ is benzyl; or wherein R¹ and R³ are each a monocarboxylic acid derivative of formula

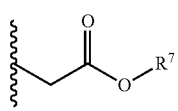

wherein R⁷ is benzyl, R² is H or —CO—CH(CH₃)₂, and R⁸ᵃ is H.

14. The compound according to claim 12, wherein the compound is represented by the structure of formula C1:

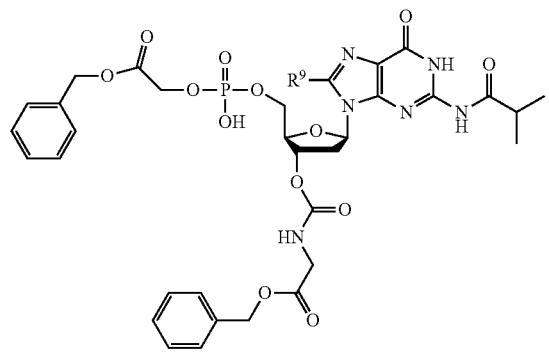

C1

15. The compound according to claim 1, which is represented by the structure of formula D:

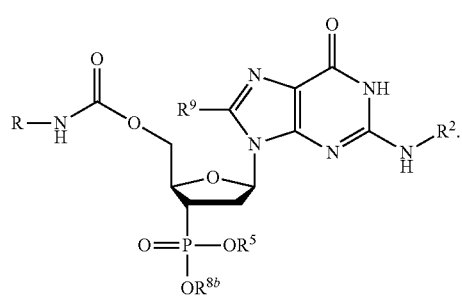

D

16. The compound according to claim 15, wherein $R^5$ is selected from the group consisting of:

(a) a monocarboxylic acid derivative of formula

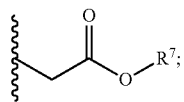

and (b) a dicarboxylic acid derivative of formula

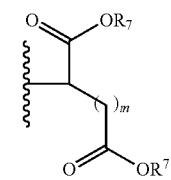

wherein m is 1 and $R^7$ is benzyl.

17. An anti-bacterial pharmaceutical composition comprising a therapeutically effective amount of a compound according to claim 1, and a pharmaceutically acceptable carrier or excipient.

18. A compound represented by the structure of formula B:

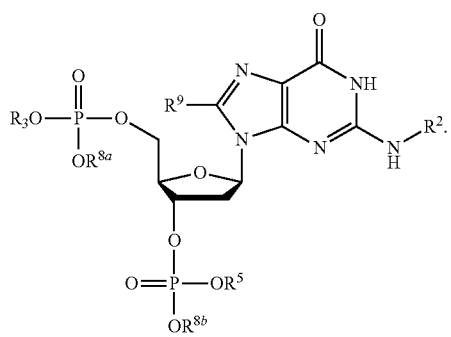

B wherein:

(i) $R^3$ and $R^5$ are each independently:

(a) a monocarboxylic acid derivative of formula

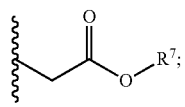

or (b) a tricarboxylic acid derivative of formula

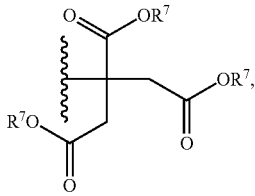

$R^2$, $R^{8a}$ and $R^{8b}$ are each H, $R^7$ is a methyl group; and $R^9$ is H, a $C_1$-$C_6$ alkyl, a $C_1$-$C_6$ alkylaryl, or an aryl; or (ii) wherein $R^3$ is a monocarboxylic acid of formula

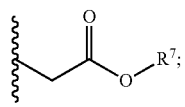

$R^2$, $R^5$, $R^{8a}$ and $R^{8b}$ are each H;

$R^7$ is methyl; and $R^9$ is H, a $C_1$-$C_6$ alkyl, a $C_1$-$C_6$ alkylaryl, or an aryl;

including salts, hydrates, solvates, polymorphs, optical isomers, geometrical isomers, enantiomers, diastereomers, complexes and mixtures thereof.

19. The compound according to claim 18, wherein the compound is represented by the structure of formula B1, B2 or B3:

B1
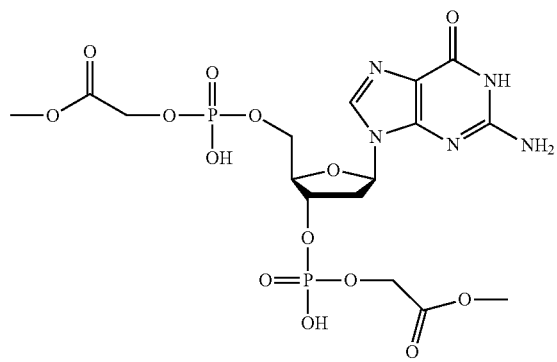
B2
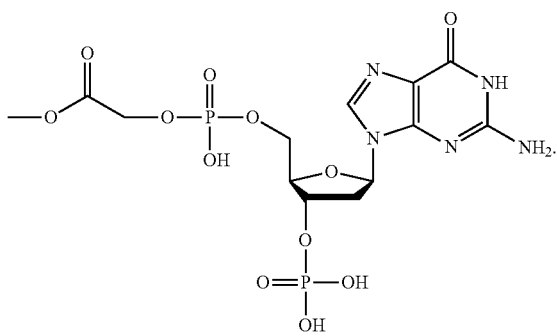
B3
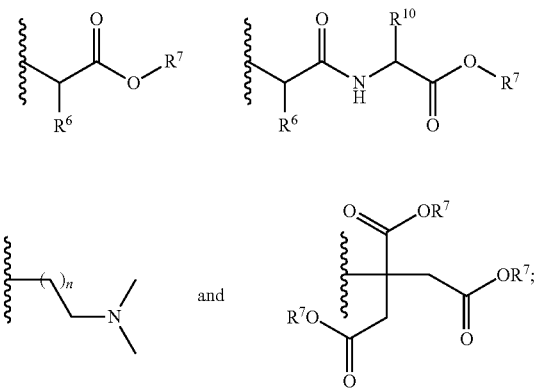
20. An anti-bacterial pharmaceutical composition comprising a therapeutically effective amount of a compound according to claim 18, and a pharmaceutically acceptable carrier or excipient.
21. A compound selected from the group consisting of:
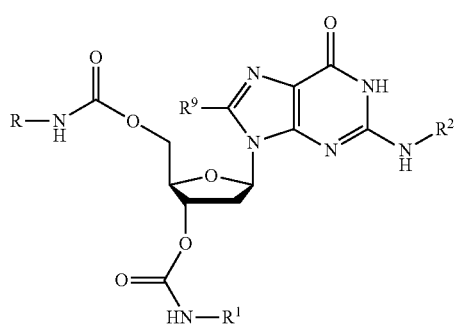
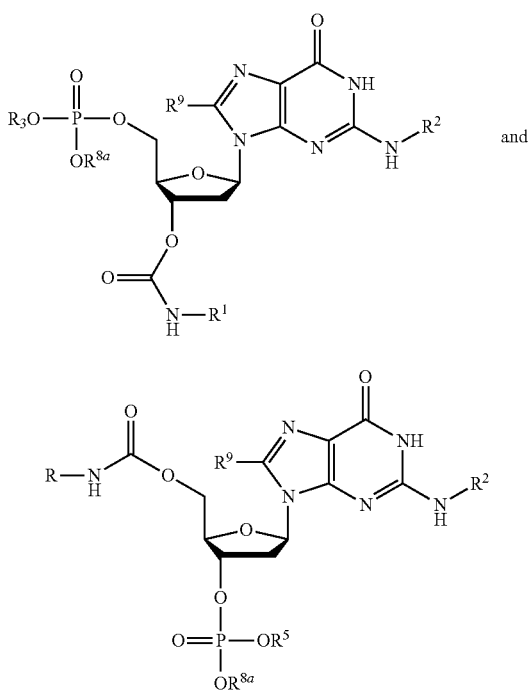
wherein:
R and $R^1$ are each independently selected from the group consisting of:

$R^2$ is H or a moiety selected from the group consisting of:

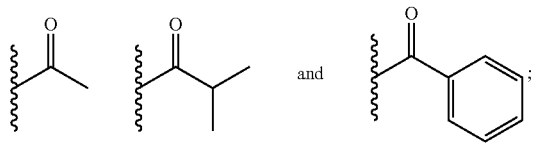

$R^3$ and $R^5$ are each independently H or a moiety selected from the group consisting of:

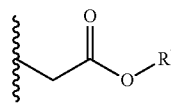  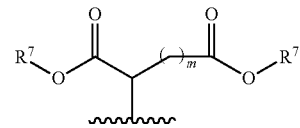

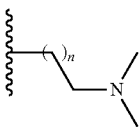 and 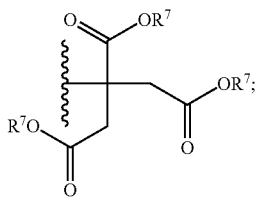

$R^6$ and $R^{13}$ are each independently a side chain of a natural or unnatural amino acid;

$R^7$ is H or a moiety selected from the group consisting of:

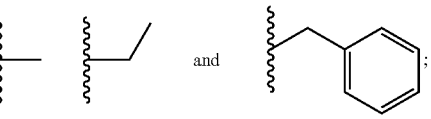

$R^{8a}$ and $R^{8b}$ are independently H or methyl; $R^9$ is H or n is 1, 2, 3, 4, 5 or 6; and
m is 1 or 2;
including salts, hydrates, solvates, polymorphs, optical isomers, geometrical isomers, enantiomers, diastereomers, complexes and mixtures thereof.

22. The compound according to claim 21, wherein $R^9$ is H.

23. The compound according to claim 21, wherein $R^9$ is phenyl.

24. A method of combating bacteria, or treating bacterial infections, comprising the step of administering to a subject in need thereof a compound according to claim 1, or a pharmaceutical composition comprising such compound.

25. A method of combating bacteria, or treating bacterial infections, comprising the step of administering to a subject in need thereof a compound according to claim 18, or a pharmaceutical composition comprising such compound.

\* \* \* \* \*

UNITED STATES PATENT AND TRADEMARK OFFICE
CERTIFICATE OF CORRECTION

PATENT NO. : 9,133,231 B2  
APPLICATION NO. : 13/813726  
DATED : September 15, 2015  
INVENTOR(S) : Wexselblatt et al.

Page 1 of 2

It is certified that error appears in the above-identified patent and that said Letters Patent is hereby corrected as shown below:

In The Claims

Column 59:  
Lines 1-18, delete formula C1 and insert the following:

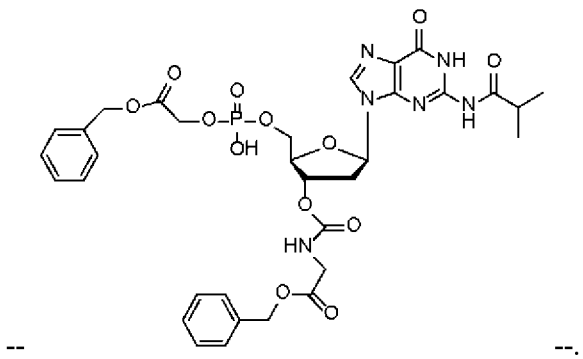

-- --.

Lines 24-34, delete formula D and insert the following:

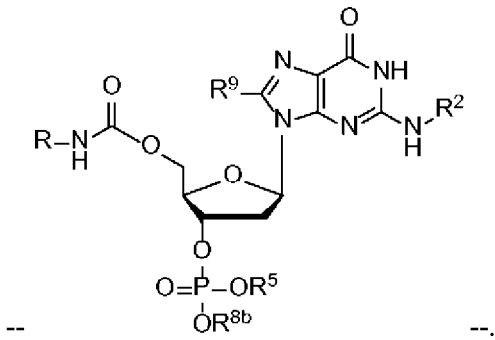

-- --.

Signed and Sealed this  
Sixteenth Day of February, 2016

Michelle K. Lee  
*Director of the United States Patent and Trademark Office*

Column 62:
Lines 33-44, delete formula D and insert the following:
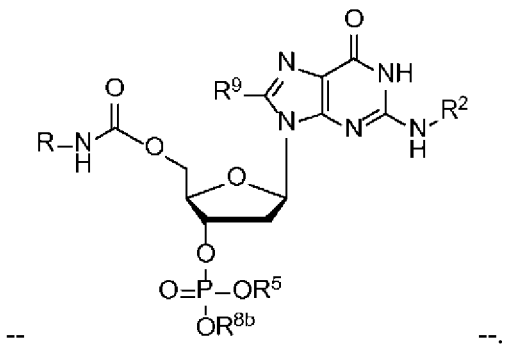
Column 63:
Line 32, after "$R^6$ and", delete "$R^{13}$" and insert -- $R^{10}$ --.